United States Patent
Zanzucchi et al.

[11] Patent Number: 5,846,396
[45] Date of Patent: Dec. 8, 1998

[54] LIQUID DISTRIBUTION SYSTEM

[75] Inventors: Peter John Zanzucchi, West Windsor Township, Mercer County; Satyam Choudary Cherukuri, Cranbury; Sterling Edward McBride, Lawrence Township, Mercer County; Robert R. Demers, Cranbury; Aaron W. Levine, Lawrenceville; Barry Jay Thaler, Lawrenceville; Robert Leon Quinn, Trenton; Paul Leonard Braun, Highland Park; William Chiang, Monmouth Junction; Zhonghui Hugh Fan, Plainsboro; Steven A. Lipp, Cranbury; James R. Matey, Mercerville, all of N.J.

[73] Assignee: Sarnoff Corporation, Princeton, N.J.

[21] Appl. No.: 556,036

[22] Filed: Nov. 9, 1995

Related U.S. Application Data

[63] Continuation-in-part of Ser. No. 338,703, Nov. 10, 1994, Pat. No. 5,585,069, and a continuation-in-part of Ser. No. 469,238, Jun. 6, 1995, Pat. No. 5,632,876, and a continuation-in-part of Ser. No. 483,331, Jun. 7, 1995, Pat. No. 5,603,351.

[51] Int. Cl.[6] .......................... G01N 27/26; G01N 21/00; B01L 11/00
[52] U.S. Cl. .......................... 204/601; 209/451; 209/454; 422/82; 422/103; 422/134; 417/50; 141/31
[58] Field of Search .............................. 422/81, 82, 100, 422/103, 102, 106, 134; 251/11; 141/31; 417/50, 474; 204/454, 451, 600, 601

[56] References Cited

U.S. PATENT DOCUMENTS

| | | | |
|---|---|---|---|
| 3,494,723 | 2/1970 | Gray | 422/21 |
| 3,615,241 | 10/1971 | Low et al. | 23/259 |
| 3,957,583 | 5/1976 | Gibson et al. | 195/10.35 R |

(List continued on next page.)

FOREIGN PATENT DOCUMENTS

| | | |
|---|---|---|
| 0 198 413 | 10/1986 | European Pat. Off. . |
| 0 402 995 | 12/1990 | European Pat. Off. . |
| 0 430248 | 6/1991 | European Pat. Off. . |
| 0 483 117 | 4/1992 | European Pat. Off. . |

(List continued on next page.)

OTHER PUBLICATIONS

Andreas Manz et al., *Trends in Analytical Chemistry*, 10(5):144–148 (1991).
Database Search * on micropumps.
Search Report for WO 93/22421, Nov. 11, 1993.
Search Report for WO 93/22055, Nov. 11, 1993.

(List continued on next page.)

*Primary Examiner*—Bruce F. Bell
*Assistant Examiner*—Alex Noguerola
*Attorney, Agent, or Firm*—William J. Burke

[57] ABSTRACT

The present invention provides a liquid distribution system, which is useful in a number of contexts, including in accomplishing various synthetic, diagnostic and drug screening reactions. The distribution system can comprise an alpha reservoir and a beta reservoir, a first set of parallel and adjacent first and second feeder channels and a second set of parallel and adjacent third and fourth feeder channels which are offset from the first and second feeder channels, wherein (a) the first and third feeder channels are connected to the alpha reservoir via a first connector channel that is situated above or below the second and fourth feeder channels and are independent of the beta reservoir and (b) the second and fourth feeder channels are connected to the beta reservoir via a second connector channel that is situated above or below the first and third feeder channels and are independent of the alpha reservoir. The distribution system is preferably a microscale distribution system. Various particular mechanisms for controlling flow into a liquid distribution system are described.

59 Claims, 16 Drawing Sheets

U.S. PATENT DOCUMENTS

| | | | |
|---|---|---|---|
| 4,038,151 | 7/1977 | Fadler et al. | 195/127 |
| 4,272,119 | 6/1981 | Columbus | 422/50 |
| 4,276,048 | 6/1981 | Leaback | 436/180 |
| 4,283,262 | 8/1981 | Cormier et al. | 207/195 M |
| 4,310,399 | 1/1982 | Columbus | 204/195 R |
| 4,385,115 | 5/1983 | de Zabala et al. | 435/33 |
| 4,412,785 | 11/1983 | Roman | 417/50 |
| 4,426,451 | 1/1984 | Columbus | 436/518 |
| 4,495,025 | 1/1985 | Haskell | 156/648 |
| 4,533,430 | 8/1985 | Bower | 156/643 |
| 4,589,952 | 5/1986 | Behringer et al. | 156/628 |
| 4,601,881 | 7/1986 | Webster | 422/67 |
| 4,676,274 | 6/1987 | Brown | 137/806 |
| 4,683,914 | 8/1987 | Brisland | 137/625.48 |
| 4,753,775 | 6/1988 | Ebersole et al. | 422/81 |
| 4,756,884 | 7/1988 | Hillman et al. | 422/73 |
| 4,891,120 | 1/1990 | Sethi et al. | 204/299 R |
| 4,908,112 | 3/1990 | Pace | 204/299 |
| 4,948,961 | 8/1990 | Hillman et al. | 250/252.1 |
| 4,960,486 | 10/1990 | Perkins et al. | 156/633 |
| 4,963,498 | 10/1990 | Hillman et al. | 436/69 |
| 4,999,283 | 3/1991 | Zavos et al. | 435/2 |
| 4,999,284 | 3/1991 | Ward et al. | 435/4 |
| 4,999,286 | 3/1991 | Gawel et al. | 435/7.32 |
| 5,000,817 | 3/1991 | Aine | 156/633 |
| 5,001,048 | 3/1991 | Taylor et al. | 435/4 |
| 5,003,822 | 4/1991 | Joshi | 73/204 |
| 5,006,749 | 4/1991 | White | 310/323 |
| 5,063,081 | 11/1991 | Cozzette et al. | 427/2 |
| 5,066,938 | 11/1991 | Kobashi et al. | 338/22 |
| 5,073,029 | 12/1991 | Eberly et al. | 356/432 |
| 5,077,017 | 12/1991 | Gorin et al. | 422/100 |
| 5,104,813 | 4/1992 | Besemer et al. | 436/179 |
| 5,112,455 | 5/1992 | Cozzette et al. | 294/153.12 |
| 5,118,384 | 6/1992 | Harmone et al. | 156/643 |
| 5,129,261 | 7/1992 | Riley | 73/313 |
| 5,129,262 | 7/1992 | White et al. | 73/599 |
| 5,140,161 | 8/1992 | Hillman et al. | 250/341 |
| 5,141,868 | 8/1992 | Shanks et al. | 435/288 |
| 5,143,854 | 9/1992 | Pirrung et al. | 436/518 |
| 5,144,139 | 9/1992 | Hillman et al. | 250/341 |
| 5,147,607 | 9/1992 | Mochida | 422/57 |
| 5,156,810 | 10/1992 | Ribi | 422/82.01 |
| 5,164,598 | 11/1992 | Hillman et al. | 250/341 |
| 5,176,203 | 1/1993 | Larzul | 165/61 |
| 5,180,288 | 1/1993 | Richter et al. | 417/48 |
| 5,186,001 | 2/1993 | Muntz | 60/515 |
| 5,188,963 | 2/1993 | Stapleton | 435/299 |
| 5,189,914 | 3/1993 | White et al. | 73/599 |
| 5,194,133 | 3/1993 | Clark et al. | 204/299 |
| 5,200,051 | 4/1993 | Cozzette et al. | 204/403 |
| 5,204,525 | 4/1993 | Hillman et al. | 250/252.1 |
| 5,212,988 | 5/1993 | White et al. | 73/599 |
| 5,220,189 | 6/1993 | Higashi et al. | 257/467 |
| 5,229,297 | 7/1993 | Schnipelsky et al. | 436/94 |
| 5,230,864 | 7/1993 | Columbus | 422/100 |
| 5,238,853 | 8/1993 | Calzi et al. | 436/68 |
| 5,241,363 | 8/1993 | Garner | 356/326 |
| 5,250,263 | 10/1993 | Manz | 422/81 |
| 5,252,743 | 10/1993 | Barrett et al. | 548/303.7 |
| 5,262,127 | 11/1993 | Wise et al. | 422/98 |
| 5,270,170 | 12/1993 | Schatz et al. | 435/7.37 |
| 5,277,754 | 1/1994 | Hadimioglu et al. | 156/644 |
| 5,279,791 | 1/1994 | Aldrich et al. | 422/58 |
| 5,288,463 | 2/1994 | Chemelli | 422/58 |
| 5,296,114 | 3/1994 | Manz | 204/180 |
| 5,296,375 | 3/1994 | Kricka et al. | 435/291 |
| 5,304,487 | 4/1994 | Wilding et al. | 435/291 |
| 5,312,590 | 5/1994 | Gunasingham | 422/56 |
| 5,324,483 | 6/1994 | Cody et al. | 422/131 |
| 5,324,633 | 6/1994 | Foder et al. | 435/6 |
| 5,359,115 | 10/1994 | Campbell et al. | 558/110 |
| 5,384,261 | 1/1995 | Winkler et al. | 436/518 |
| 5,412,087 | 5/1995 | McGall et al. | 536/24.3 |
| 5,420,328 | 5/1995 | Campbell | 538/110 |
| 5,424,186 | 6/1995 | Fodor et al. | 435/6 |
| 5,427,946 | 6/1995 | Kricka et al. | 435/291 |
| 5,463,564 | 10/1995 | Agrafiotis et al. | 364/496 |
| 5,480,614 | 1/1996 | Kamahori | 422/70 |
| 5,580,523 | 12/1996 | BArd | 422/50 |

FOREIGN PATENT DOCUMENTS

| | | |
|---|---|---|
| 3811052 C2 | 8/1989 | Germany . |
| 2248840 | 4/1992 | United Kingdom . |
| WO 90/09596 | 8/1990 | WIPO . |
| WO 91/16966 | 11/1991 | WIPO . |
| WO 92/10092 | 6/1992 | WIPO . |
| WO 93/06121 | 4/1993 | WIPO . |
| WO 93/22058 | 11/1993 | WIPO . |
| WO 94/05414 | 3/1994 | WIPO . |
| WO 94/10128 | 5/1994 | WIPO . |
| WO 95/12608 | 5/1995 | WIPO . |

OTHER PUBLICATIONS

Search Report for WO 93/22054, Nov. 11, 1993.

Search Report for WO 93/22053, Nov. 11, 1993.

Gazette entry for Tsui et al., Variable Range Position Indicator, U.S. Patent No. 5,345,215, Jun. 17, 1993.

Gazette entry for Murphy et al., Automated Capillary Scanning System, U.S. Patent No. 5,009,003, Feb. 14, 1990.

Woolley et al., Ultra–High Speed DNA Fragment Separations Using Microfabricated Capillary Array Electrophoresis Chips, Proc. Natl. Acad. Sci. USA 91:11348–11352, Nov. 1994.

Dasgupta et al., Electroosmosis: A Reliable Fluid Propulsion System for Flow Injection Analysis, Anal. Chem. 66:1792–1798, 1994 no month available.

Harmon et al., Selectivity in Electrophoretically Mediated Microanalysis by Control of Product Detection Time, Anal. Chem. 66:3797–3805, 1994 no month available.

Patterson, et al., Electrophoreically Mediated Microanalysis of Calcium, Journal of Chromatography A, 662:389–395, 1994.

Microfabricated Device is Chemistry Lab on a Chip, Chemical & Engineering News, Dec., 1991.

Harmon et al., Mathematical Treatment of Electrophoretically Mediated Microanalysis, Anal. Chem. 65:2655–2662, 1993 no month availble.

Avila and Whitesides, Catalytic Activity of Native Enzymes During Capillary Electrophoresis: An Enzymatic Microreactor, J. Org. Chem. 58:5508–5512, 1993 no month availble.

Harmon, et al., Electrophoretically Mediated Microanalysis of Ethanol, J. Chormatog. A, 657:429–434, 1993 no month avaible.

Bao and Regnier, Ultramicro Enzyme Assays in a Capillary Electrophoretic System, J. Chrom. 608:217–224, 1992 no month available.

Richeter et al., A Micromachined Electrohydynamic (EHD0 Pump, Sensors and Actuators A, 29:159–168, 1992 no month available.

Bart et al., Microfabricated Electrohydrodynamic Pumps, Sensors and Actuators, A21–A23:193–197, 1990 no month available.

Melcher, Traveling–Wave Induced Electroconvection, The Physics of Fluids, 9:1548–1555, 1966 no month available.

Pickard, Ion Drag Pumping, I. Theory, J. Applied Physics 34:246–250, 1963.

Pickard, Ion Drag Pumping. II. Experiment, J. Applied Physics, 34:251–258, 1963 no month available.

Stuetzer, Ion Drag Pumps, J. Applied Physics, 31:136–146, 1960 no month available.

Tracey, et al., Microfabricated Microhaemorheometer, pp. 82–84, 1991 no month available.

Medynski, Synthetic peptide Combinatorial Libraries, Bio/Technology, vol. 12, Jul. 1994.

Jacobson et al., Precolumn Reations with Electrophoretic Analysis Integrated on a Microchip, Anal, Chem., 66:4127–4132 no month available.

Jacobson, et al., Effects of Injection Schemes and Column Geometry on the Performance of Microchip Electrophoresis Devices, Anal. Chem. 1994, 66:1107–1113 no month available.

Jacobson, et al., High–Speed Separations on a Microchip, anal. Chem. 1994, 66:1114–1118 no month available.

Fan, et al., Micromachining of Capillary Electrophoresis Injectors and Separators on Glass Chips and Evaluation of Flow at Capillary Intersections, Anal. Chem., 1994, 6:177–184 no month available.

Megregany, Microeletromechanical Systems, Circuits and Devices, Jul. 1993.

Harrison, et al., Micromachining a Miniaturized Capillary Electrophoresis–Based Chemical Analysis System on a Chip, Science, vol. 261, Aug. 13, 1993.

Harrison, et al., Capillary Electrophoresis and Sample Injection Systems Integrated on a Planar Glass Chip, Anal. Chem. 1992, 64:1926–1932 no month available.

Fisher, Microchips for Drug Compounds, New York Times, Mar. 3, 1991.

Fodor, ete al., Light–Directed, Spatially Addressable Parallel Chemical Synthesis, Research Article, Science, vol. 251, Feb. 15, 1991, pp. 767–773.

The Silver Shotguns, The Economist, Dec. 14–20, 1991.

Howe, et al., Silicon Micromechanisms; Sensors and Actuators on a Chip, IEEE Spectrum, Jul. 1990.

Wenzel, et al., A Multisensor Employing an Ultrasonic Lamb–Wave Oscillator, IEEE Transactions on Electron Devices, vol. 35, No. 5, Jun. 1988.

Angell, et al., Silicon Micromechanical Devices, Scientific American 248:44–55, 1983 no month available.

Petersen, Silicon as a Mechanical Material, Proceedings of the IEEE, vol. 79, No. 5, May. 1982.

Dialog Search, May 18, 1994.

BArt et al. (Sensors and Actuators, "Microfabricated Electrohydrodynamic Pumps", A21–A23 (1990). no month available.

Richter et al. (Sensors and Actuators, "A Micromachined Electrohydrodynamic (EHD) Pump", A29(1991)159–168) no month available.

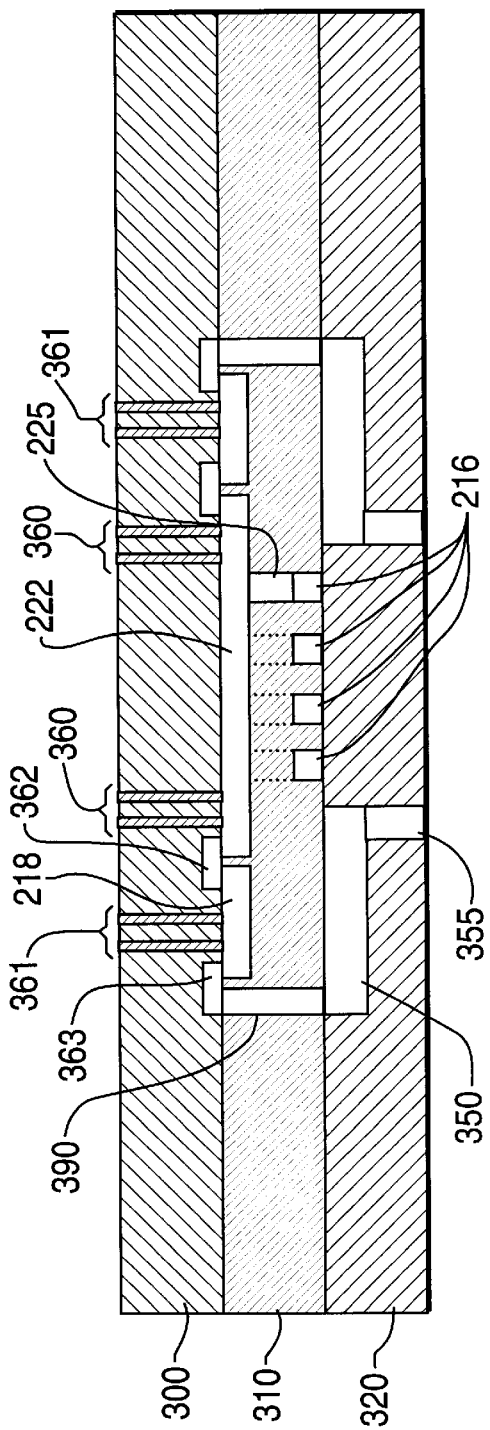
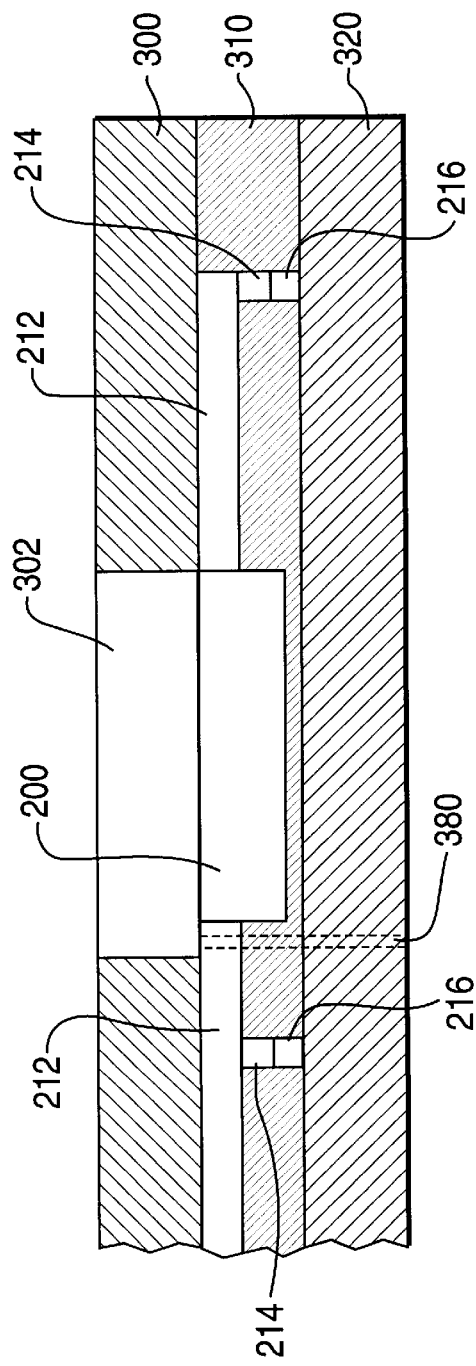

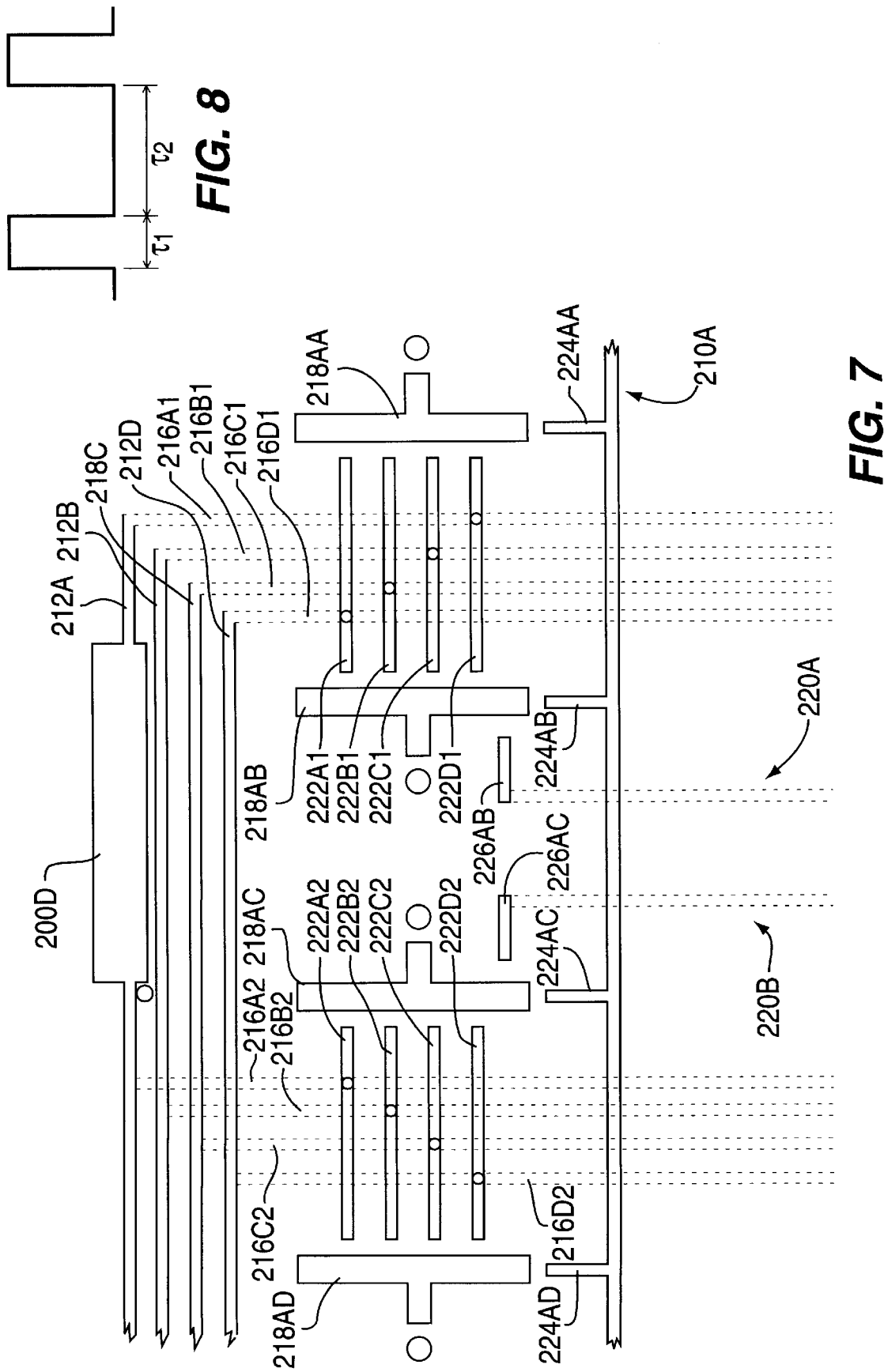

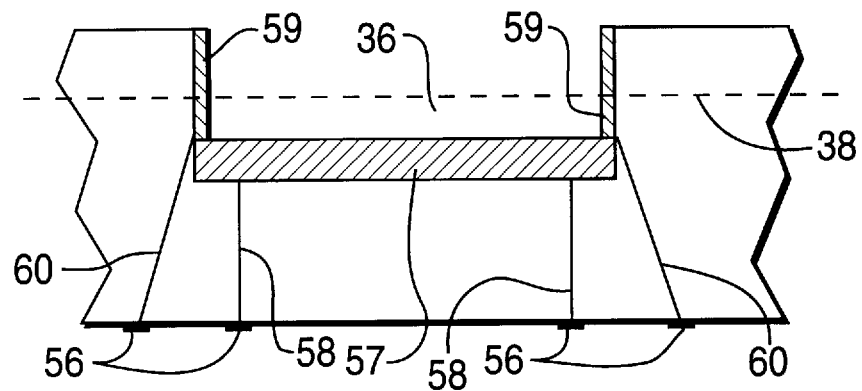
FIG. 20
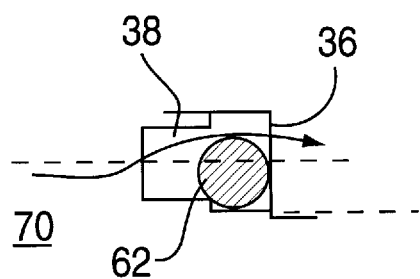 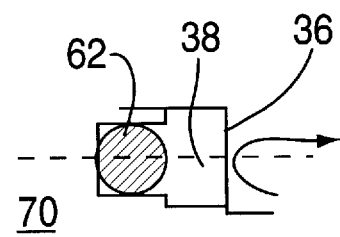
FIG. 21A     FIG. 21B

LIQUID DISTRIBUTION SYSTEM

This application is a continuation-in-part of U.S. application Ser. No. 08/338,703, titled "A Partitioned Microelectronic and Fluidic Device Array for Clinical Diagnostics and Chemical Synthesis," filed Nov. 10, 1994, a continuation-in-part of U.S. application Ser. No. 08/469,238, titled "Apparatus and Methods for Controlling Fluid Flow in Microchannels," filed Jun. 6, 1995 now U.S. Pat. No. 5,632,876 and a continuation-in-part of U.S. application Ser. No. 08/483,331, titled "Method and System for Inhibiting Cross-Contamination in Fluids of Combinatorial Chemistry Device," filed Jun. 7, 1995, now U.S. Pat. No. 5,603,351.

This application relates to a method and system for manipulating fluids, which is useful in a number of contexts, including in accomplishing various synthetic, diagnostic and drug screening reactions. More particularly, this invention relates to a system and method, which incorporates a layered array, for distributing reagent liquids while inhibiting the contamination or cross-contamination of these liquids.

Recently, a number of academic articles have focused on the problems associated with conducting chemical reactions on a micro-scale. This literature has discussed the possibility of managing such reactions on wafer-sized solid supports that have been etched to create microchannels. Reactor systems of this scale could allow multiple diagnostic or drug screening assays to be conducted in a transportable device that uses small amounts of reagents, thus reducing supply and disposal costs.

One mechanism for developing new drugs not provided for by nature has been dubbed "rational" drug design. This process looks at the structures of biological macromolecules as determined by crystallography and at the structures of pharmacological agents known to interact with these macromolecules. With the use of computer workstations, it was hoped that new pharmacological agents could be designed that had appropriately positioned functionalities for strongly interacting with the macromolecule. One difficulty with this approach is that growing crystals appropriate for crystallographic structural determinations is a tedious, empirical science. In many cases, it is unclear if appropriate crystals can be grown (for instance, for the glycoprotein hormones such a chorionic gonadotropin or other glycoproteins). Another difficulty is that chemistry does not provide the malleable construction tools evoked by the phrase "design"; instead, chemical building blocks provide only a limited number of bond angles and lengths. For example, the structural routes by which a chlorine group might be positioned in particular part of a drug-binding pocket in the macromolecule may be many, while the advantages or disadvantages of the ancillary structures needed to position this group are hard to "rationally" evaluate.

Combinatorial chemistry seeks to create its own "evolutionary" process that selects, from pools of compounds, compounds with the desired pharmacological activity. The key to making the process evolutionary is to generate large families of "mutants", in this case families of compounds with some chemical relatedness but with clear differences. The concepts of rational design may be taken advantage of in selecting the families of compounds to be explored by the combinatorial method.

Combinatorial chemistry seeks to generate new leads to classes of compounds that have potential pharmacological activity. Traditionally, such leads have been found by screening various plant or animal extracts for pharmacological activity. Such extracts are tedious to obtain, may have very small concentrations of potentially useful compounds, and at best only contain compounds selected by evolutionary pressures that may have nothing to do with the disease that is sought to be treated. After an extract has been identified, the process provides little information as to the identity of the active ingredient.

Combinatorial chemistry seeks to create the large, diverse family of compounds by permutation of a relatively limited set of building block chemicals. Preferably, the combinatorial method will create identifiable pools containing one or more synthetic compounds. These pools need not be identifiable by the chemical structure of the component compounds, but should be identifiable by the chemical protocol that created the compounds. These pools are then screened in an assay that is believed to correlate with a pharmacological activity. Those pools that produce promising results are examined further to identify the component compounds and to identify which of the component compounds are responsible for the results.

The follow-up protocol used to identify the active compounds in a combinatorial pool can also involve a combinatorial method. For instance, the promising pool could result from the reaction, first, of a mixture of compounds A, B and C, which compounds do not react with one another, with compounds D, E and F, which compounds do not react with one another but do react with compounds A, B or C. Second, the resulting compounds are reacted with compounds G, H and I. To narrow the possible identity of the active compounds in the pool, the A-D, A-E, A-F, B-D, B-E, B-F, C-D, C-E and C-F products can be separately created by combinatorial chemistry and separately reacted with a the mixture of G, H and I. After this step, the sub-pool that is active in the screening assay generally will contain a more limited family of compounds.

Once promising molecules are identified by combinatorial chemistry, the identified molecules provide information that aides in the design of further combinatorial experiments. The full array of promising compounds identified by combinatorial chemistry can provide valuable information to guide traditional pharmaceutical chemistry efforts.

A popular tool in the emerging field of combinatorial chemistry is to attach the first chemical building blocks to solid support, typically a glass or polymeric support, such as the supports used in the well known Merrifield method for synthesizing polypeptides. This attachment provides a mechanism for quickly isolating product by simply washing away reactants and related impurities and decoupling the product from the support. In some cases, the support-coupled product can be assayed for pharmacological activity.

Miniaturization is usefully employed in combinatorial chemistry since: (i) workers generally seek compounds that are pharmacologically active in small concentrations; (ii) in creating a vast "evolutionary" assortment of candidate molecules it is preferable to have the numerous reactions well documented and preferably under the direction of a limited number of workers to establish reproducibility of technique; (iii) it is expensive to create a vast, traditionally-scaled synthetic chemistry complex for creating a sufficiently diverse family of candidate compounds; and (iv) substantial concerns are raised by the prospect of conducting assays of the products of combinatorial chemistry at more standard reaction scales. Miniaturization allows for the economic use of robotic control, thereby furthering reproducibility.

The wafer-sized devices described above can be ideal for combinatorial chemistry, allowing for numerous synthetic chemistry reactions to be conducted substantially under computer control using only small quantities of reagents. However, the academic literature advocating such micro-scale devices has not adequately addressed fundamental issues in conducting combinatorial chemistry at this scale: for instance, how does one manage to shuttle reagents through a complex microscale device and accomplish this without significant cross-contamination while allowing a complex assortment of different syntheses to occur in a large number of microscale reaction vessels (e.g., 100 to 10,000) in the device? The present invention provides a microscale device that solves these issues.

SUMMARY OF THE INVENTION

The present invention provides a liquid distribution system, which is useful in a number of contexts, including accomplishing various synthetic, diagnostic and drug screening reactions. The distribution system can comprise an alpha reservoir and a beta reservoir, a first set of parallel and adjacent first and second feeder channels and a second set of parallel and adjacent third and fourth feeder channels which are offset from the first and second feeder channels, wherein (a) the first and third feeder channels are connected to the alpha reservoir via a first connector channel that is situated above or below the second and fourth feeder channels and are independent of the beta reservoir and (b) the second and fourth feeder channels are connected to the beta reservoir via a second connector channel that is situated above or below the first and third feeder channels and are independent of the alpha reservoir. The distribution system is preferably a microscale distribution system.

BRIEF DESCRIPTION OF THE DRAWINGS

FIG. 6A shows a cross-section along an EW axis through a distribution channel.

FIG. 6B shows a cross-section along an EW axis through a first reservoir.

FIG. 7 is a top view of a part of a distribution plate.

FIG. 8 shows a voltage pulse pattern used to power an electrode-based pump useful in the liquid distribution system of the invention.

FIG. 20 shows a reaction cell having a heater and a thermocouple.

FIGS. 21A and 21B show a valve design.

DEFINITIONS

Figure 1:
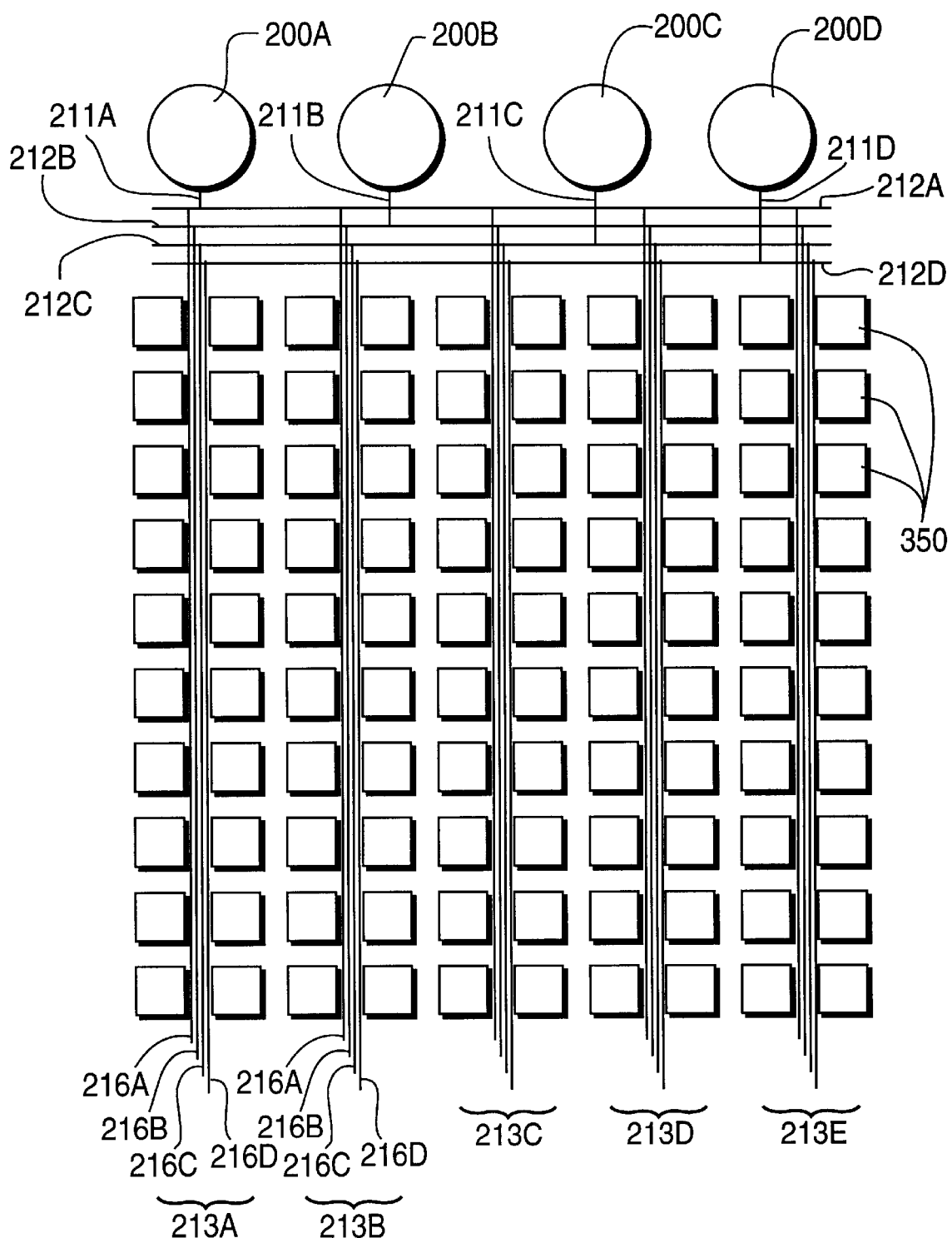
FIG. 1 shows a system of channels for addressing any of one hundred reaction cells with any of four fluids.

The following terms shall have the meaning set forth below:

| | |
|---|---|
| addressable | a reaction cell or channel is "addressable" by a reservoir or another channel if liquid from the reservoir or other channel can be directed to the reaction cell or channel. |
| adjacent | "adjacent" as used in these situations: (i) a first structure in one of the plates is adjacent to a second structure in the same or another plate if the vertical projection of the first structure onto the plate of the second structure superimposes the first structure on the second or places it within about 250 $\mu$m of the second; and (ii) groupings of two or more channels are adjacent to one another if each channel is in substantially the same horizontal plane, and all but the outside two channels in the grouping are adjacent (in the sense defined in (i) above) to two neighbor channels in the grouping. Preferably, under item (i), a first structure is adjacent to a second structure if the vertical projection of the first structure onto the plate of the second structure superimposes the first structure on the second or places it within about 150 $\mu$m of the second. |
| capillary dimensions | dimensions that favor capillary flow of a liquid. Typically, channels of capillary dimensions are no wider than about 1.5 mm. Preferably channels are no wider than about 500 $\mu$m, yet more preferably no wider than about 250 $\mu$m, still more preferably no wider than about 150 $\mu$m. |
| capillary barrier | a barrier to fluid flow in a channel comprising an opening of the channel into a larger space designed to favor the formation, by liquid in the channel, of an energy minimizing liquid surface such as a meniscus at the opening. Preferably, capillary barriers include a dam that raises the vertical height of the channel immediately before the opening into the larger space. |
| connected | the channels, reservoirs and reaction cells of the invention are "connected" if there is a route allowing fluid between them, which route does not involve using a reaction cell as part of the link. |
| continuous flow channel | a channel having an overflow outlet allowing for fluid to continuously flow through the channel. |
| directly connected | reservoirs and horizontal channels are "directly connected" if they are connected and either (1) no other channel is interposed between them or (2) only a single vertical channel is interposed between them. |
| expansion valve | an expandable chamber, associated with a fluid channel, which chamber (a) is filled with a gas or a liquid with a boiling point within about 10° C. of the intended operating temperature of the liquid distribution system and (b) has an associated heater element for heating the expandable chamber to boil the liquid or expand the gas to cause sufficient expansion of the expandable chamber to fill a cross-section of the fluid channel. |

-continued

| | |
|---|---|
| hole diameter | because techniques for fabricating small holes often create holes that are wider at one end than the other (for instance, about 50 microns wider), the hole diameter values recited to herein refer to the narrowest diameter. |
| horizontal, vertical, EW, NS | indications of the orientation of a part of the distribution system refer to the orientation when the device is in use. The notations "EW axis" and "NS axis" are in reference to FIGS. 1, 2, 3 and 7, where an EW axis goes from right to left and is perpendicular to the long axis of the page and a NS axis is from top to bottom parallel to the long axis of the page. |
| independent | channels, reservoirs or reaction cells that are not connected. |
| offset | two sets of channels are "offset" when none of the channels in the first such set is adjacent to any of the channels in the second set. |
| open zone | a region of a channel that widens to decrease the flow-induced pressure of a fluid flowing through the channel. |
| perpendicular | channels in the distribution plate are perpendicular even if primarily located on separate horizontal planes if their vertical projections onto the same horizontal plane are perpendicular. |
| reservoir | unless a different meaning is apparent from the context, the terms "reservoir" and "fluid reservoir" include the horizontal extension channels (sometimes simply termed "extensions") directly connected to the reservoir or fluid reservoir. |
| second reservoir extension channels | these extension channels include the distribution channels that may branch off of these extension channels |
| substantially the length of one of the horizontal dimensions | at least about 70% of on of the major horizontal dimensions (e.g. the EW or NS dimensions illustrated in the Figures) of the distribution plate. |
| U-plumbing channel | a channel designed to connect at least two channels or reservoirs such that the liquid level in one of the connected channels or reservoirs will equalize with the liquid level in the other connected channel or reservoirs due to hydrological forces. U-plumbing channels typically have vertical channels that connect channels or reservoirs located in a higher vertical plane with a substantially horizontal channel segment of the U-plumbing channel located in a lower plane -- these vertical and horizontal segments together comprise the U-plumbing channel. The feeder channels of the invention are typically U-plumbing channels. |

DETAILED DESCRIPTION

One version of the invention is a hydrologic liquid distribution system comprising: a distribution plate comprising: a least two first reservoirs having a common first fill level; at least one feeder channel connected to and extending from each of the first reservoirs, each feeder channel having a horizontal feeder channel segment, wherein the top of the horizontal feeder channel segment is below the first fill level; at least one distribution channel connected to each feeder channel having a second fill level at substantially the same elevation as the first fill level; and a first liquid level maintaining means for maintaining the liquid level in each first reservoir at the first fill level, wherein filling each first reservoir to the first fill level results in the filling of the connected feeder channels and filling the connected distribution channels to the second fill level. The distribution channels preferably have at least one capillary barrier.

The distribution plate is preferably coupled with a feedthrough plate that fits above the distribution plate and provides channels or conduits to allow for the passage of liquids or electrical leads through to the distribution plate. A detachable reaction cell plate is preferably coupled underneath the distribution plate and contains one or more, more preferably two or more, reaction cells into which liquids from at least two reservoirs may be distributed via the distribution plate. The reaction cell plate preferably contains about 100 or more reaction cells, each addressable by at least two reservoirs. More preferably the reaction cell plate contains about 1,000 or more reaction cells, each addressable by at least two reservoirs. Yet more preferably the reaction cell plate contains about 10,000 or more reaction cells, each addressable by at least two reservoirs.

The distribution plate preferably has multiple first reservoirs. The first reservoirs can have a primary reservoir portion and one or more first reservoir extension channels, which preferably together extend along substantially the length of one of the horizontal dimensions of the distribution plate. Two or more such extended first reservoirs are preferably adjacent and parallelly arrayed along one side of the distribution plate. In some embodiments, it is desirable to relay liquid from two or more of such parallel, extended first reservoirs to each of two or more reaction cells arrayed along a substantially straight line (the "linear" reaction cells). To accomplish this liquid relay, preferably a first feeder channel extends from the parallel first reservoir nearest the edge of the distribution plate and underneath the interiorly located parallel first reservoirs, while separate, feeder channels, located adjacent to and parallel to the first feeder channel, extend from the interiorly located parallel first reservoirs passing beneath other first reservoirs as needed to maintain the segregation of the liquids in the reservoirs. In this preferred embodiment, arrayed adjacent to the location of each of the linear reaction cells are one distribution channel for each such first reservoir, each such distribution channel connected to a separate one of the parallel feeder channels. Thus, the distribution channels located adjacent to a reaction cell form a "bundle" of distribution channels. Using pumps located in each of the bundled distribution channels and conduits from each bundled distribution channel to the adjacent reaction cell, liquid from each of the separate first reservoirs can be distributed to any of the linear reaction cells.

Each distribution channel preferably includes at least one pump, which preferably comprises two or three electrodes. To operate the pumps in an appropriate sequence, the distribution system of the invention is preferably connected to a controller that controls each of the pumps. The preferred two electrode pumps preferably are operated by applying a pulsed voltage program appropriate for moving the liquid sought to be pumped. Preferably, the controller includes a data storage device comprising a database of pumping programs designating parameters, such as the pulse length, voltage amplitude, pulse shape and voltage polarity, suitable for moving each of a plurality of liquids.

The invention further relates to a preferential flow liquid distribution system, which is suitable, for example, for conducting reactions for chemical syntheses or chemical reactions involved in an assay, the distribution system comprising: two or more continuous flow channels, each having a upstream end and a downstream end, wherein the continuous flow channels have an open zone at the downstream end; for each continuous flow channel, a branch channel extending off of that continuous flow channel in the open zone; and, for each continuous flow channel, an alpha constrictor for constricting flow in the open zone, the alpha constrictor located downstream of the branch channel inlet, wherein when a liquid flows through one of the continuous flow channels from the first to the second end a first ratio amount of fluid is diverted into the branch channel when the alpha constrictor is not operating and a second ratio amount, which is greater than the first ratio amount, flows into the branch channel when the alpha constrictor is in operation. Preferably, the branch channel inlets are within about 300 microns of the upstream point at which the open zone begins. Preferably, the distribution system has, for at least one branch channel, a beta constrictor for constricting flow through the branch channel. In another preferred embodiment, the distribution system has a buffer channel addressable by at least two continuous flow channels via their associated branch channels.

The invention additionally relates to a expansion valve liquid distribution system made up of a reaction cell, two or more feeder channels, a separate conduit for each feeder channel connecting that feeder channel to the reaction cell, and a expansion valve for each conduit, wherein the expansion valve has an expanded state that fills a cross-section of the conduit and prevents fluid flow through the conduit and an contracted state that allows fluid flow through the conduit. In a preferred embodiment, conduits have two or more, preferably three or more, expansion valves which can be operated in concert to pump liquid from the connected feeder channel into the reaction cell.

The invention further relates to a electrode-based liquid distribution system made up of (a) one or more, preferably two or more, feeder channels each made up of a feeder channel inlet and a feeder channel outlet and, connected to each such feeder channel, a distribution channel, each feeder channel having a three-way junction connecting a feeder channel inlet, a feeder channel outlet and the connected distribution channel, the distribution channel connecting with a reaction cell, (b) for each such three-way junction, a first electrode-based pump in the feeder channel inlet or in the feeder channel outlet and (c) for each such three-way junction, a second electrode-based pump in the distribution channel, wherein the voltages applied to the first electrode-based pump and the second electrode-based pump can be chosen (i) so that fluid in one of the feeder channels can be moved from the feeder channel inlet to the feeder channel outlet of the feeder channel without substantial flow into the connected distribution channel or (ii) so that a substantial amount of flow proceeds via the connected distribution channel.

A. A Basic Liquid Distribution System

Figure 2:
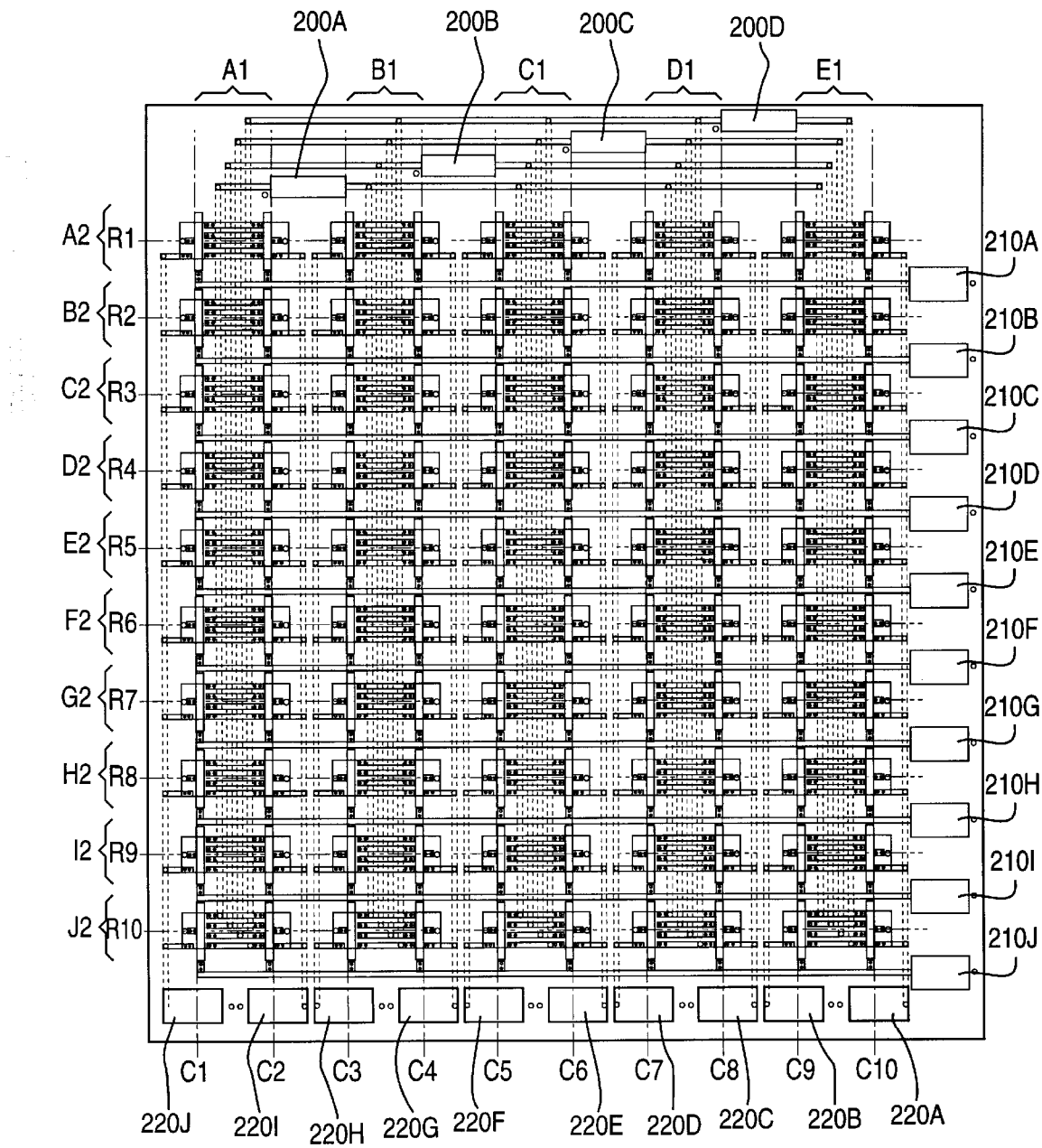
FIG. 2 displays a distribution plate according to the invention.

The invention relates to methods of addressing a large number of reaction cells 350 with a plurality of fluid reservoirs 200 (see FIGS. 1 and 2). In FIG. 1, reservoirs 200A–200D are connected to reservoir extension channels 212A–212D via first connector channels 211A–211D, respectively. The ceilings of first connector channels 211A–211D are located in a lower horizontal plane than the floors of extension channels 212A–212D, thereby assuring, for instance, that fluid from reservoir 200B does not leak into the extension channel 212A connected to reservoir 200A. Each first connector channel 211A–211D connects with its respective reservoir extension 212A–212D via vertical channels (not illustrated). Connected to extension channels 212A–212D are first, second, third, fourth and fifth sets 213A–213E of first, second, third and fourth feeder channels 216A–216D. The ceilings of these feeder channels are located in a horizontal plane beneath the floors of the extension channels 212A–212D. Via these extension channels, fluid from each of the four first fluid reservoirs 200A–200D can be brought to a location adjacent to any of the one hundred reaction cells 350 into which the fluid can be moved under the control of pumps or valves as described hereinbelow. Note that reaction cells 350 are located in a lower horizontal plane than first, second, third and fourth feeder channels 216A–216D. Other geometries by which a large number of reaction cells can be addressed by separated fluid reservoirs are described below.

Features of other distribution systems described in this application can be applied to this embodiment, irrespective of under which subheading they are described. It will be understood by those of ordinary skill that while the embodiments of the invention are described with reference to channels that join at orthogonal angles, other angles are possible. In preferred embodiments of the invention, the operational flow rate (i.e., the flow rate when the appropriate flow-inducing mechanisms are activated) from a given reservoir (e.g. first fluid reservoir 200) to a given reaction cell 350 is from about 0.01 $\mu$l/min to about 10 $\mu$l/min, more preferably from about 0.1 $\mu$l/min to about 0.3 $\mu$l/min.

B. Hydrologic Liquid Distribution System
i. the distribution, feedthrough and reaction cell plates Typically, the liquid distribution system of the invention will be formed of at least three plates, a feedthrough plate 300, a distribution plate 310 and a reaction cell plate 320. The feedthrough plate 300 is typically bonded to the distribution plate 310 using one of the methods described below. The reaction cell plate 320 is typically removably fitted to the underside of the distribution plate 310, or the underside of intermediate plate 330 (not illustrated) interposed between the distribution plate 310 and the reaction cell plate 320.

Figure 3:
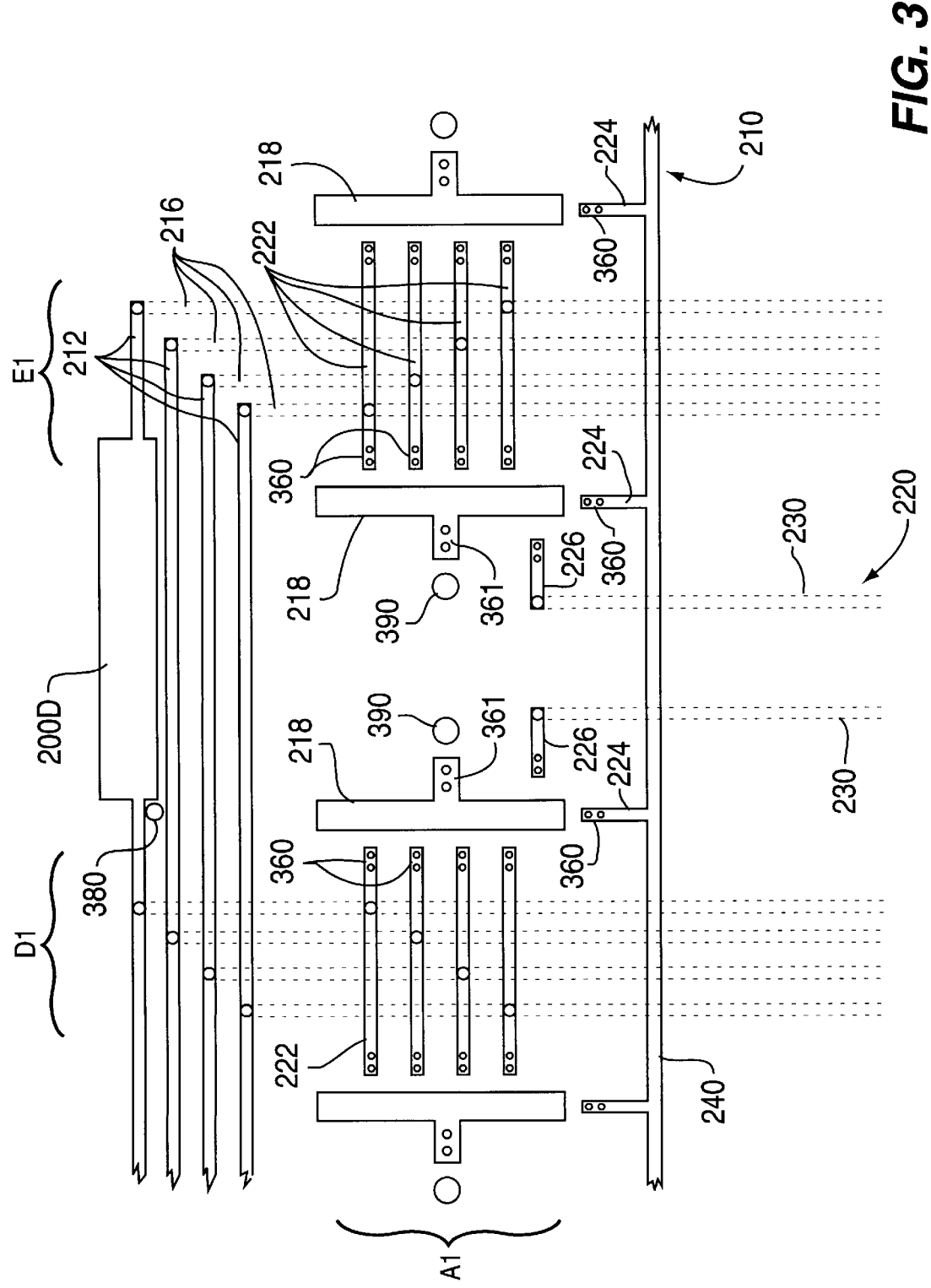
FIG. 3 displays an expanded view of a portion of the distribution plate of FIG. 1.

FIG. 2 shows the layout of a distribution plate 310 according to the invention. FIG. 3 shows an expanded view of a portion of a distribution plate 310 that better illustrates some of the features obscured by the scale of FIG. 2. Typically, the structures indicated in solid lines will be formed in the top layer of the distribution plate 310, while the structures indicated with dotted lines will be formed in the bottom layer of the distribution plate 310, except that in FIG. 2 the reaction cells 350 are indicated by boxes in solid lines even though these structures are located in a lower plane . Where appropriate, vertical channels connect the structures in the top of the distribution plate 310 with those in the bottom. For convenience, the axis from the top of the illustration to the bottom is designated the NS axis, while the axis from right to left is the EW axis.

At the top of FIG. 2 are four first fluid reservoirs 200A, 200B, 200C and 200D, each having a defined fill level. Each of these first fluid reservoirs 200A, 200B, 200C and 200D has two first reservoir extensions 212 extending along substantially all of an EW axis of the distribution plate 310. The ceilings of the first reservoir extensions 212 preferably are at substantially the same elevation as the first fill level. At five staggered locations, A1, B1, C1, D1 and E1, along the EW axis of the first reservoir extensions 212 there are four first vertical channels 214 (see FIGS. 5 and 6B) that connect the first reservoir extensions 212 with four first horizontal feeder channel segments 216 that are formed in the bottom layer of the distribution plate 310. At each staggered location A1, B1, C1, D1 or E1, four adjacent first horizontal feeder channel segments 216, which are connected to separate first reservoir extensions 212, extend along an NS axis to ten positions, A2, B2, C2, D2, E2, F2, G2, H2, I2 and J2. Each position A2, B2, C2, D2, E2, F2, G2, I2 or J2 along the course of each such set of four adjacent horizontal feeder channel segments 216 is adjacent to a pair of reaction cells 350 (see FIGS. 5 and 6B). At these positions A2, B2, C2, D2, E2, F2, G2, H2, I2, or J2, the four adjacent first horizontal feeder channel segments 216 are separately connected, via separate second vertical channels 225 (see FIGS. 4A, 4B, 5 and 6A), to each of four perpendicular first distribution channels's 222 formed in the top layer of the distribution plate 310. The ceilings of the first distribution channels 222 define a second fill level that is typically substantially the elevation of the first fill level. The fill level of a distribution channel (e.g., the second fill level) is "substantially" the fill level of the connected reservoir (e.g., the first fill level) if they are offset vertically by no more than about 10% of the depth of the channel; even if the fill levels are further offset vertically they are still substantially the same if filling the reservoir to its fill level results in filling the connected distribution channel and the retention of fluid in the connected distribution channel (for instance, retention due to the capillary barriers described further below with reference to FIG. 4A). The combination of a first vertical channel 214, connected to a horizontal feeder channel segment 216, in turn connected to a second vertical channel 225 makes up a first feeder channel 217 (not identified in the Figures).

If liquids are maintained at a defined first level in a first fluid reservoir 200, then substantially the same level will be maintained in the first distribution channels 222 connected to that first fluid reservoir 200 via first feeder channels 217. This equalization occurs due to the principle that two connected bodies of liquid will tend to seek the same level and, where the size of the channels allows, due to capillary flow. Liquids are maintained at a defined level in the first fluid reservoirs. In the illustrated embodiment, liquid is fed into the fluid reservoir 200 through channels in the feedthrough plate 300 and such liquid that is not needed to fill the fluid reservoirs to the defined level is drained through drains 380. First openings 381 (not shown) are formed in the bottom layer of the feedthrough plate 300 to create a liquid connection or sluice between the first fluid reservoirs 200 and the drains 380. Liquids are constantly feed into the first fluid reservoirs 200 (as well as the second fluid reservoirs 210 and third fluid reservoirs 220) typically by the use of an external pump 15 (not shown), such as the model number 205U multichannel cassette pump available from Watson-Marlow, Inc. Alternatively, a defined level can be maintained by monitoring the level of liquid in the first fluid reservoirs 200 (or second fluid reservoirs 210 or third fluid reservoirs 220) and only activating the pumps feeding liquid to a given fluid reservoir when needed to maintain the defined level.

Each set of four adjacent first distribution channels 222 are adjacent to two "buffer" or "intermediary" channels 218, located to each side of the first distribution channels 222 along the EW axis. Liquid can be pumped from any first distribution channel 222 into the adjacent buffer channel 218 by activating the first pump 360 (indicated in FIG. 3 by two filled dots representing the electrodes of one type of pump) of the first distribution channel 222. This pumping creates additional pressure that moves the liquid over capillary barrier 370 (see FIGS. 4A, 4B and 5) separating the first distribution channel 222 and the buffer channel 218. Between each first distribution channel 222, second distribution channel 224 or third distribution channel 226 and the adjacent buffer channel 218 and between each buffer channel 218 and its adjacent third vertical channel 390 (described below) there is such a capillary barrier 370 that inhibits liquid flow when the pumps are not activated. Second openings 362 (see FIGS. 4A and 4B) are formed in the bottom layer of the feedthrough plate 300 to create a liquid connection or sluice between the first distribution channels 222 and the buffer channels 218. From a buffer channel 218, liquid can be pumped using a second pump 361 (indicated in FIG. 3 by two filled dots representing the electrodes of one type of pump) to a third vertical channel 390 that connects with a reaction cell in the reaction cell plate 320. Third openings 363 (see FIGS. 4A and 4B) in the bottom layer of the feedthrough plate 300 or the distribution plate 310 serve to create a liquid connection or sluice between the buffer channels 218 and third vertical channels 390.

Figure 4A:
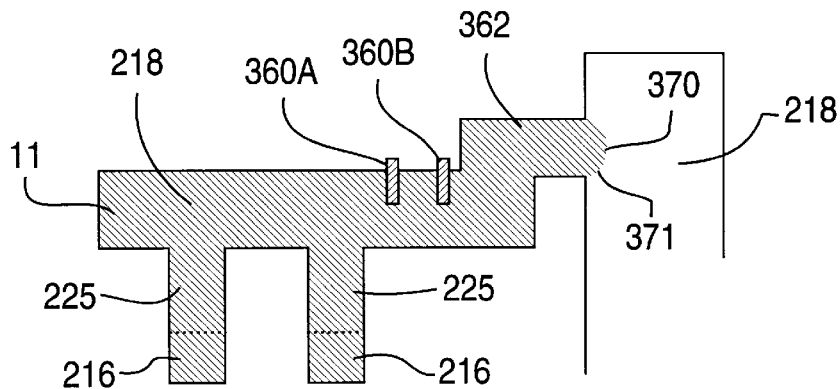
FIG. 4A shows a capillary barrier between a first distribution channel and a buffer channel.
Figure 4B:
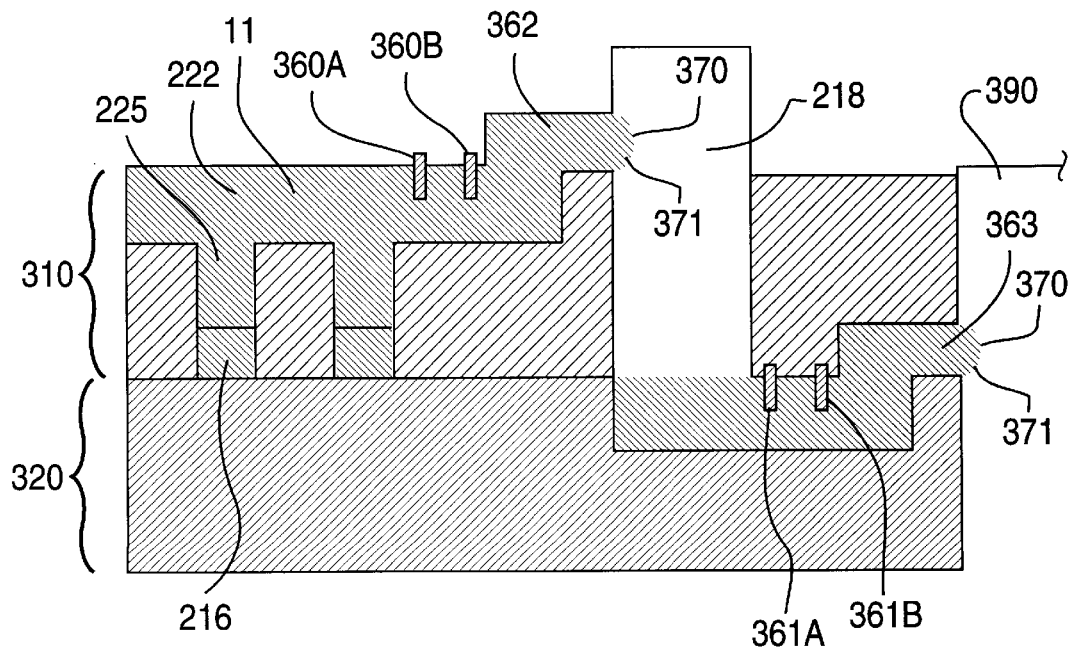
FIG. 4B shows a capillary barrier between a first distribution channel and a buffer channel and another capillary barrier between a buffer channel and a vertical channel.

FIG. 4A illustrates a capillary barrier 370, at which a meniscus 371 forms, at the junction between a first distribution channel 222 containing liquid 11 and either a buffer channel 218 or a third vertical channel 390. The meniscus 371 formed at the outlet of first distribution channel 222 into buffer channel 218 will tend to inhibit seepage from the first distribution channel 222, such as the seepage that can result from capillary forces. FIG. 4B shows, in a variation of the distribution system illustrated in FIGS. 2 and 3, capillary barriers 370 at the junction between first distribution channel 222 and buffer channel 218 and at the junction between buffer channel 218 and third vertical channel 390. Also shown are first electrode 360A and second electrode 360B making up first pump 360 and third electrode 361A and fourth electrode 361B making up pump 361. In some embodiments there are vents (not illustrated) that extend through the feedthrough plate 300 at the tops of buffer channel 218 or third vertical channel 390.

Note that only a small cut-away of NS oriented horizontal feeder channel segments 216 are shown in FIGS. 4A and 4B. Typically, these channels extend inwardly and outwardly from the illustrated cut-away and connect with additional first distribution channels 222 situated to distribute liquid to other reaction cells 350.

Along the right side of the distribution plate 310 are ten second fluid reservoirs 210, each having a second reservoir extension 240 extending along an EW axis. Second distribution channels 224 form "L"-extensions off of second reservoir extensions 240 and are each positioned adjacent to a separate buffer channel 218, such that there are ten second distribution channels 224 extending off of each second reservoir extension 240. Each second distribution channel 224 has a pump 360 that can move liquid from a second distribution channel 224 to the adjacent buffer channel 218. Second openings 362 (not shown) in the bottom of feedthrough plate 300 serve to provide a sluice or route of liquid connection between the second distribution channels 224 and the buffer channels 218. Liquid moves from the buffer channels 218 to the reaction cells as described above. Located adjacent to each second reservoir 210 is a drain 380 (not shown) that operates to maintain a defined third fill level as described above.

As will be described further below in Section H in reference to FIGS. 16A–16D, the capillary barriers 370 and sluices created by the second openings 362 or third openings 363 act as a combined valve and pump. The capillary barriers 370 prevent flow to the reaction cell, which flow would be favored by capillary forces, until the first pumps 360 or second pumps 361 provide the extra pressure needed to overcome the capillary barriers 370. Narrowing the sluices can increase the capillary forces favoring flow, thereby reducing the amount of added pressure needed to overcome the capillary barriers 370. The use of the capillary barriers 370 allows flow control to be governed by the first pumps 360 or second pumps 361, which are typically controlled by controller 10.

Located along the bottom edge of the distribution plate illustrated in FIG. 2 are ten third liquid fluid reservoirs 220.

Horizontal feeder channel segments 230 are connected to the third fluid reservoirs 220 20 and to third distribution channels 226 via fourth vertical channels 227. The third distribution channels 226 have first pumps 360 which can move liquid into adjacent buffer channels 218 via openings 362 (not shown) in the feedthrough plate 300. Located adjacent to each third fluid reservoir 220 is a drain 380 (not shown) that operates to maintain a defined fourth fill level as described above. Third fluid reservoirs 220 and connected third distribution channels 226 operate in just the same way as first fluid reservoirs 200 and first distribution channels 222. Those of ordinary skill in the art will readily envision alternative geometries wherein a number of separate third fluid reservoirs 220 can interact with a given buffer channel 218 via a number of third distribution channels 226 positioned adjacent to the buffer channel 218. Located adjacent to each third reservoir 220 is a drain 380 (not shown) that operates to maintain a defined third fill level as described above.

Figure 5:
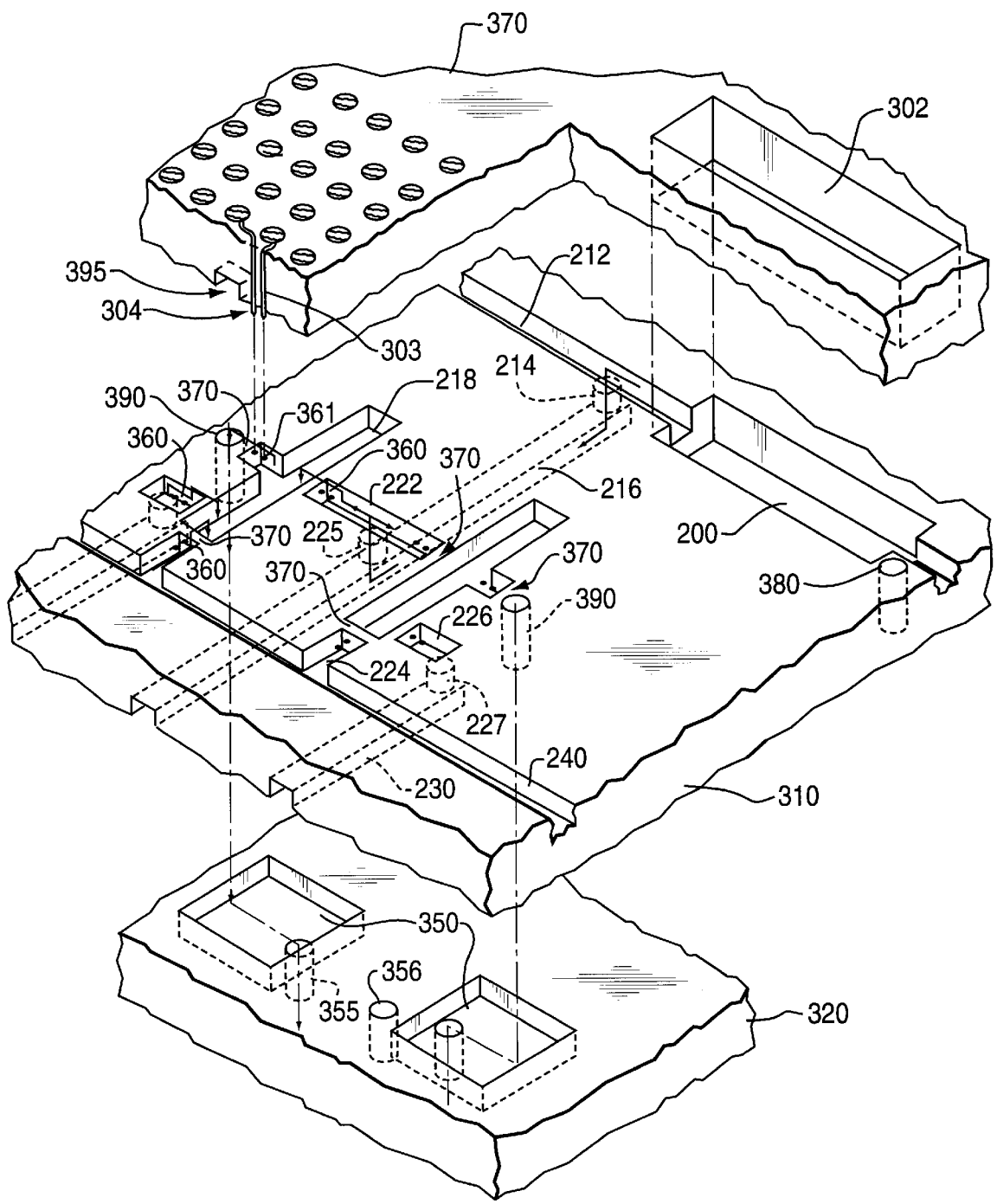
FIG. 5 shows in three dimensions various cut-away views of the feedthrough plate, distribution plate and reaction cell plate of a distribution system of the invention.

FIG. 5 shows perspective views of portions of feedthrough plate 300, distribution plate 310 and reaction cell plate 320.

FIG. 6A shows a vertical cross-section along an EW axis that slices through a first distribution channel 222. Underneath the first distribution channel 222 can be seen four horizontal feeder channel segments 216, only one of which is connected to the first distribution channel via visible second vertical channel 225. Leads 303 and 304 which connect the electrodes of the first pumps 360 and second pumps 361 are illustrated. Third vertical channel 390 connects buffer channel 218 to reaction cell 350, which has a drain 355.

FIG. 6B shows a vertical cross-section along an EW axis that slices through a first fluid reservoir 200. From first fluid reservoirs extensions 212 can be seen two first vertical channels 214 that each connect to a separate horizontal feeder channel segment 216. Drain 380 for first fluid reservoir 200 is indicated by dotted lines. In the illustrated distribution system, first fluid reservoir 200 opens to the top of feedthrough plate 300 via fourth openings 302.

The operation of the liquid distribution system can be described with reference to FIG. 7. Liquid can be distributed to first reaction cell 350AA (not shown) connected to third vertical channel 390A from any of first, second or third fluid reservoirs 200A, 200B, 200C, 200D, 210A or 220A. If "liquid A" is maintained at first fluid level in fluid reservoir 200A, liquid A will flow through the connected vertical channels 214 into the connected horizontal feeder channel segments 216A, 216A2, 216A3, 216A4 and 216A5 and into the connected distribution channels 222A1, 222A2, and so on. From first distribution channel 222A1, liquid A is pumped into first buffer channel 218AA using pump 360A under the control of controller 10 (not shown). From first buffer channel 218AA, liquid A is pumped into first reaction cell 350AA via third vertical channel 390A using pump 361A under the control of controller 10.

When a distribution plate 310 according to the invention makes use of a buffer channel 218 and the buffer channel 218 lacks a vent to the outside atmosphere, the relationship between the pumping rate of a first pump 360 that pumps liquid into the buffer channel 218 and the pumping rate of a second pump 361 that pumps liquid from the buffer channel 218 to a reaction cell 350 can be manipulated to advantage. When a first pump 360 moves liquid from, for instance, distribution channel 222A1 (FIG. 7), a pressure increase is created in buffer channel 218 which inhibits flow past the capillary barriers for distribution channels 222B1, 222C1, 222D1, 224AA and 226AA. A delay in the corresponding activation of second pump 361 will result in this cross-contamination inhibiting pressure being maintained. The buffer channel 218 further serves to dilute any accidental overflows from distribution channels containing reagents not intended for the adjacent reaction cell 350. This dilution will typically reduce the concentration of reactive reagents beneath the concentration effective in the reaction process that is intended for the adjacent reaction cell 350.

Note that in the illustrated embodiment, each of six solutions or solvents can be distributed to each of one hundred reaction cells 350 from first, second and third fluid reservoirs 200A, 200B, 200C, 200D, 210 and 220. Each of the ten second fluid reservoirs 210, or each of the ten third fluid reservoirs 220, can contain a separate solution or solvent intended for use in the ten associated reaction cells that can be addressed by the fluid reservoir. The four first fluid reservoirs 200A, 200B, 200C and 200D each can address any of the one hundred reaction cells 350. Further flexibility is available by flushing a given fluid reservoir with a new solution or solvent when appropriate during a protocol.

Note that the buffer channels 218 are optional. Buffer channels 218 can be avoided by providing for direct conduits from the outlets of distribution channels (which outlets are preferably capillary barriers 370) to the appropriate reaction cell 350.

The fluid reservoirs (e.g. first, second and third fluid reservoirs 200, 210 and 220) are typically simply expanded (i.e. wider) portions of the attached extension channels. Preferably, the liquid in the fluid reservoirs is maintained within ±10% f the difference between the floor of the fluid reservoir and its fill level. Replenishment of the liquid in the reservoirs can be continuous, step-wise on a defined schedule, or based on sensor data feed to controller 10. The drains 380 are designed to remove any excess fluid added to the reservoir by use of external pump 15. The fluid reservoirs, filled to the respective fill level, preferably have a volume from about 1 $\mu$l to about 5 $\mu$l, more preferably about 02.5 $\mu$l. Thus, in the more preferred embodiment, the volume in the fluid reservoirs will preferably be 2.5 $\mu$l±0.25 $\mu$l. Appropriate peristaltic pumps, such as the model number 205U multichannel cassette pump available from Watson-Marlow, Inc., can deliver liquid at rates as low as 1 $\mu$l per second. Such pumps need only be activated for a fraction of a second to adequately recharge a fluid reservoir.

The above discussion describes the distribution system as being formed with a feedthrough plate 300, distribution plate 310 and reaction cell plate 320. However, it will be clear that additional plates can conveniently be incorporated into the distribution system. For instance, a intermediate plate 330 is, in a preferred embodiment, permanently bonded underneath the distribution plate 310 and interposed between the distribution plate 310 and the reaction cell plate 320. The use of the intermediate plate 330 allows for much greater flexibility in the design of the channels the form the distribution system.

ii. the pumps

Any pumping device of suitable dimensions can be used as the internal first pumps 360 or second pumps 361 in the liquid distribution system of the invention. Such pumps can include microelectromechanical systems (MEMS) such as reported by Shoji et al., "Fabrication of a Pump for Integrated Chemical Analyzing Systems," *Electronics and Communications in Japan*, Part 2, 70: 52–59, 1989 or Esashi et al., "Normally closed microvalve and pump fabricated on a Silicon Wafer," *Sensors and Actuators*, 20: 163–169, 1989 or piezo-electric pumps such as described in Moroney et al., "Ultrasonically Induced Microtransport," *Proc. MEMS*, 91: 277–282, 1991. Preferably, however, the first pumps 360 and second pumps 361 have no moving parts. Such first pumps 360 or second pumps 361 can comprise electrode-based pumps. At least two types of such electrode-based pumping has been described, typically under the names "electrohydrodynamic pumping" (EHD) and "electroosmosis" (EO). EHD pumping has been described by Bart et al., "Microfabricated Electrohydrodynamic Pumps," *Sensors and Actuators*, A21–A23: 193–197, 1990 and Richter et al., "A Micromachined Electrohydrodynamic Pump," *Sensors and Actuators*, A29:159–168, 1991. EO pumps have been described by Dasgupta et al., "Electroosmosis: A Reliable Fluid Propulsion System for Flow Injection Analysis," *Anal Chem.*, 66: 1792–1798, 1994.

EO pumping is believed to take advantage of the principle that the surfaces of many solids, including quartz, glass and the like, become charged, negatively or positively, in the presence of ionic materials, such as salts, acids or bases. The charged surfaces will attract oppositely charged counter ions in solutions of suitable conductivity. The application of a voltage to such a solution results in a migration of the counter ions to the oppositely charged electrode, and moves the bulk of the fluid as well. The volume flow rate is proportional to the current, and the volume flow generated in the fluid is also proportional to the applied voltage. Typically, in channels of capillary dimensions, the electrodes effecting flow can be spaced further apart than in EHD pumping, since the electrodes are only involved in applying force, and not, as in EHD, in creating charges on which the force will act. EO pumping is generally perceived as a method appropriate for pumping conductive solutions.

EHD pumps have typically been viewed as suitable for moving fluids of extremely low conductivity, e.g., $10^{-14}$ to $10^{-9}$ S/cm. It has now been demonstrated herein that a broad range of solvents and solutions can be pumped using appropriate solutes than facilitate pumping, using appropriate electrode spacings and geometries, or using appropriate pulsed or d.c. voltages to power the electrodes, as described further below.

The electrodes of first pumps 360 and second pumps 361 used in the liquid distribution system preferably have a diameter from about 25 microns to about 100 microns, more preferably from about 50 microns to about 75 microns. Preferably, the electrodes protrude from the top of a channel to a depth of from about 5% to about 95% of the depth of the channel, more preferably from about 25% to about 50% of the depth of the channel. Usually, as a result the electrodes, defined as the elements that interact with fluid, are from about 5 microns to about 95 microns in length, preferably from about 25 microns about to 50 microns. Preferably, a pump includes an alpha electrode 364 (such as first electrode 360A or third electrode 361A) and a beta electrode 365 (such as third electrode 360B and fourth electrode 361B) that are preferably spaced from about 100 microns to about 2,500 microns apart, more preferably, from about 250 microns to about 1000 microns apart, yet more preferably, from about 150 microns to about 250 microns apart. The separation of electrodes is measured from the center points of the electrodes as they first protrude into their associated fluid channel. In a particularly preferred embodiment, a gamma electrode 366 (not shown) is spaced from about 200 microns to about 5,000 microns, more preferably from about 500 microns to about 1,500 microns, yet more preferably about 1,000 microns from the farther of the alpha electrode 364 and the beta electrode 365. In an alternative preferred embodiment, the pump has two additional electrodes comprising a gamma electrode 366 (not shown) and a delta electrode 367 that are spaced from about 200 microns to about 5,000 microns, more preferably from about 500 microns to about 1,500 microns, yet more preferably about 1,000 microns apart. Where the electrodes are located in fluid channels that have bends, the distances are measured along a line that defines the center line of the fluid channel. In contexts where relatively low conductivity fluids are pumped, voltages are applied across the alpha electrode 364 and the beta electrode 365, while in contexts where relatively more highly conductive fluids are pumped the voltage is induced between gamma electrode 366 and one of alpha electrode 364, beta electrode 365 or delta electrode 367. The latter circumstance typically applies for solvents traditionally pumped with EO pumping, although this invention is not limited to any theory that has developed around the concepts of EHD or EO pumping. No firm rules dictate which electrode combination is appropriate for a given solvent or solution; instead an appropriate combination can be determined empirically in light of the disclosures herein.

The voltages used across alpha and beta electrodes 364 and 365 when the pump is operated in d.c. mode are typically from about 50 V to about 2,000 V, preferably from about 100 V to about 750 V, more preferably from about 200 V to about 300 V. The voltages used across gamma electrode 366 and alpha, beta or delta electrodes 364, 365 or 367 when the pump is operated in d.c. mode are typically from about 50 V to about 2,000 V, preferably from about 100 V to about 750 V, more preferably from about 200 V to about 300 V. The voltages used across alpha and beta electrodes 364 and 365 when the pump is operated in pulsed mode are typically from about 50 V to about 1,000 V, preferably from about 100 V and about 400 V, more preferably from about 200 V to about 300 V. The voltages used across gamma electrode 366 and the alpha, beta or gamma electrode 364, 365 or 367 when the pump is operated in pulsed mode are typically from about 50 V to about 1,000 V, preferably from about 100 V and about 400 V, more preferably from about 200 V to about 300 V. Preferably, the ratio of pumping to current will be such that no more than about one electron flows into the solution adjacent to a first pump 360 or second pump 361 for every 1,000 molecules that move past the pump 360 or 361, more preferably for every 10,000 molecules that move past the pump 360 or 361, yet more preferably for every 100,000 molecules that move past the pump 360 or 361.

It is believed that an electrode-based internal pumping system can best be integrated into the liquid distribution system of the invention with flow-rate control at multiple pump sites and with relatively less complex electronics if the pumps are operated by applying pulsed voltages across the electrodes. FIG. 8 shows an example of a pulse protocol where the pulse-width of the voltage is $T_1$ and the pulse interval is $T_2$. Typically, $T_1$ is between about 1 $\mu$s and about 1 ms, preferably between about 0.1 ms and about 1 ms. Typically, $T_2$ is between about 0.1 $\mu$s and about 10 ms, preferably between about 1 ms and about 10 ms. A pulsed voltage protocol is believed to confer other advantages including ease of integration into high density electronics (allowing for hundreds of thousands of pumps to be embedded on a wafer-sized device), reductions in the amount of electrolysis that occurs at the electrodes, reductions in thermal convection near the electrodes, and the ability to use simpler drivers. The pulse protocol can also use pulse wave geometries that are more complex than the block pattern illustrated in FIG. 8.

Another, procedure that can be applied is to use a number of electrodes, typically evenly spaced, and to use a travelling wave protocol that induces a voltage at each pair of adjacent electrodes in a timed manner that first begins to apply voltage to the first and second electrodes, then to the second and third electrodes, and so on. Such methods are described in Fuhr et al., *J. Microelectrical Systems*, 1: 141–145, 1992. It is believed that travelling wave protocols can induce temperature gradients and corresponding conductivity gradients that facilitate electric field-induced fluid flow. Such temperature gradients can also be induced by positioning electrical heaters in association with the electrode-based first pumps 360 and second pumps 361.

While not wishing to be restricted to theory, several theoretical concepts are believed to play a role in the mechanics of EHD pumping. The forces acting on a dielectric fluid are believed to be described by:

$$\overline{F} = q\overline{E} + \overline{P}\nabla\overline{E} - \frac{1}{2} E^2 \nabla \epsilon + \nabla \left[ \frac{1}{2} \rho \frac{\partial e}{\partial \rho} E^2 \right]$$

where F is the force density, q is the charge density, E is the applied field, P is the polarization vector, $\epsilon$ is the permittivity and $\rho$ is the mass density. Of the terms in the equation, the first and third are believed to be the most significant in the context of EHD pumping of fluids. The first term (qE) relates to the Coulomb interaction with a space-charge region. The third term ($\frac{1}{2}E^2\nabla\epsilon$) relates to the dielectric force which is proportional to the gradient in permittivity.

In low fields, i.e., the Ohmic region where current is linearly proportional to voltage, the primary source of charges that will be acted upon by the electric field are believed to be primarily due to ions from additives, ions from impurities and ions formed by autodissociation of molecules in the fluid. In intermediate fields, i.e. from beyond the Ohmic region to about 2 V/$\mu$m, the charges are believed to be primarily formed by dissociation and electrolylytic processes in the fluid. In higher fields, the charges are believed to be determined by injection processes at the electrodes, which electrodes inject homocharges.

For the purposes of this application, positive (+) flow shall be flow in the direction of the negative electrode, and negative (−) flow shall be flow in the direction of the positive electrode.

In a preferred embodiment of the invention, the controller 10 has a device for storing data and stores the values of voltage and polarity suitable for pumping a number of solvents.

Experimental results indicate that the properties of fluid flow (like direction of flow) correlate well with the solvent's ability to stabilize and solvate the charged species injected or induced from the electrodes. The direction of flow is believed to be determined by the preference of the solvent to solvate either positive charges or negative ions. This salvation preference is believed to imply a greater shell of solvent molecules that will be dragged in an electric field, creating fluid movement, when a field is applied to the electrodes of a first pump 360 or a second pump 361. For example, a preferred salvation of positive charges correlates with a preference for fluid flow from the anode to the cathode (i.e., the positive direction). The degree of such a solvation preference for a solvent is believed to depend on the ability of the molecules within the solvent to accept or donate hydrogen bonds. In one aspect of the invention, for liquids whose pumping behavior has not yet been characterized, the controller will store initial pumping parameters estimated using on the Linear Solvation Energy relationships established by R. W. Taft and co-workers. See, Kamlet et al., *J. Org. Chem.*, 48: 2877–2887, 1983 and Kamlet et al., *Prog. Phys. Org. Chem.*, 13: 485, 1981. These workers have categorized solvents in terms of the following parameters: $\pi$, the ability of the solvent to stabilize a stabilize a charge or dipole by virtue of its dielectic properties; $\alpha$, the hydrogen bond donating ability of the solvent; and $\beta$, the hydrogen bond accepting ability of the solvent. These parameters are more fully defined in the above-cited Kamlet et al. publications, from which these definitions are incorporated herein by reference.

Using a one mm capillary of circular cross-section, a pair of 50 micron rod-shaped, platinum electrodes perpendicularly inserted to a depth of 500 microns into the capillary with a 500 micron separation powered by a 400 V field, the direction of flow was determined for several solvents. The direction of flow and the $\alpha$, $\beta$, $\pi$, $\epsilon$ and dipole moment values are as follows:

| Solvent | direction | $\alpha$ | $\beta$ | $\pi$ | $\epsilon$ | dipole moment |
|---|---|---|---|---|---|---|
| ethanol | − | 0.83 | 0.77 | .54 | 24.55 | 1.69 |
| tetrahydro-furan | + | 0 | 0.55 | .58 | 7.58 | 1.75 |
| chloroform | − | 0.44 | 0 | .58 | 4.806 | 1.01 |
| acetone | + | 0.08 | 0.48 | .71 | 20.7 | 2.69 |
| methanol | − | 0.93 | 0.62 | .6 | 32.7 | 2.87 |
| 2-propanol | +/− | 0.76 | 0.95 | .48 | 19.92 | 1.66 |
| acetonitrile | + | 0.19 | 0.31 | .75 | 37.5 | 3.92 |
| N-methyl-pyrrolidone | + | 0 | 0.77 | .92 | 32.0 | 4.09 |
| diethyl ether | + | 0 | 0.47 | 0.27 | 4.335 | 1.15 |
| 1,2 dichloro ethane | − | 0 | 0 | 0.81 | 10.36 | 1.2 |
| DMF | + | 0 | 0.69 | .88 | 36.71 | 3.86 |

It is believed that the $\alpha$ and $\beta$ values reflect the ability of the solvent under an electric field to solvate a negative or positive charged species, with the magnitude of $\alpha$–$\beta$ correlating with (−) flow, and the magnitude of $\beta$–$\alpha$ correlating with (+) flow. According to one aspect of the invention, the preferred direction of flow of a liquid can be reversed from that predicted as above if the fluid has a difference in $\alpha$ and $\beta$ values that is small but not zero and the electrode pair used creates an asymmetric field, such that the acting force on either positive or negative charged species is enhanced. One such electrode pair has an alpha electrode 364 with a sharp point pointing in the direction of intended flow and a beta electrode 365 that lines the walls of the channel in which it is located. Such an electrode-based pump, fabricated in a 1 mm capillary, has been shown to be effective to pump 2-propanol in the direction pointed to by the alpha electrode 364 either when the voltage applied to the electrodes implied a (−) direction of flow or, with somewhat weaker flow, when the voltage applied to the electrodes implied a (+) direction of flow.

The pumping parameters of a liquid can be calibrated using a plug of the liquid disposed in a capillary that has an electrode-based pump and is angled uphill. If optical devices are associated with the capillary for monitoring the position of the plug, the velocity of pumped flow uphill and the velocity of gravity driven downhill motion can be measured. With these velocities and the angle of the capillary, the pressure applied to the liquid can be calculated. (Fluid resistance, $R = (8 \cdot \mu \cdot l)/\pi^4$, where $\mu$ defines viscosity and l=the length of the fluid plug; Pressure, $P = RA(v_{up} - v_{down})$, where A =cross-sectional area). The efficiency of the pump can also be calculated ($\eta = (q \cdot \rho \cdot Q \cdot N_A)/m \cdot l$, where $\rho$=charge of e−, $\rho$=density of liquid, Q=flow rate=$v_{up} \cdot A$, m=mass of liquid, and l=current). The velocities can be measured with multiple single point observations of the location of either the front or rear interfaces of the plug using fixed LEDs and optical detectors or in a continuous mode using a light and a silicon photodiode position sensor, such as a SL15 or SC10 position sensor available from UDT Sensors, Inc., Hawthorne, Calif. With the latter method, the correlation between the signal produced at the difference amplifier connected to the position sensor must be calibrated prior to experimental use.

The pumping parameters for a number of solvents have been determined in the 1 mm capillary described above, as follows:

| Solvent | Flow rate, Q $\mu$l/sec | Pressure, P $N/m^2$ | electrical efficiency, $\eta$, molecules/e$^-$ |
|---|---|---|---|
| acetone | 14.56 | 16.33 | $1.9 \times 10^6$ |
| methanol | 24.46 | 26.32 | $9.7 \times 10^4$ |
| 1-propanol | 16.39 | 74.89 | $4.2 \times 10^5$ |
| diethyl ether | 18.44 | 20.45 | $5.8 \times 10^8$ |
| 1,2 dichloroethane | 14.24 | 46.55 | $2.9 \times 10^7$ |

Another aspect of pumping is the observation that fluids that are resistant to pumping at a reasonable field strength can be made more susceptible to electrode-based pumping by adding a suitable flow-enhancing additive. Preferably, the flow-enhancing additive is miscible with the resistant fluid and can be pumped at high pressure, P, high flow rate, Q, and good electrical efficiency, $\eta$ (i.e., molecules pumped per electron of current). Generally, the flow-enhancing additive comprises between about 0.05% w/w and about 10% w/w of the resistant fluid, preferably between about 0.1% w/w and about 5% w/w, more preferably between about 0.1% w/w and about 1% w/w. Carbon tetrachloride and cyclohexane do not pump using the electrode pump situated in a capillary described above at a voltage of 2,000 V. By adding 0.5% w/w acetone or methanol as a flow-enhancing additive, both of these fluids can be pumped at a voltage of 1,000 V. In some cases, it is desirable to reverse the preferred flow direction of a liquid by mixing with it a flow-enhancing additive that strongly pumps in the desired direction. In all cases, additives are selected on the basis of their pumping characteristics and their compatibility with the chemistries or other processes sought to be achieved in the liquid distribution system.

The electrode-based pumps of the invention can be operated to as a valve to resist flow in a certain direction by operating the pumps to counter the unwanted flow. To power the electrode-based pumps, one or more digital drivers, consisting of, for example, a shift register, latch, gate and switching device, such as a DMOS transistor, permits simplified electronics so that fluid flow in each of the channels can be controlled independently. Preferably, each digital driver is connected to multiple switching devices that each can be used to control the pumping rate of a separate electrode-based pump.

Features of other distribution systems described in this application can be applied to this embodiment, irrespective of under which subheading they are described.

C. Preferential Flow Liquid Distribution System

Figure 9:
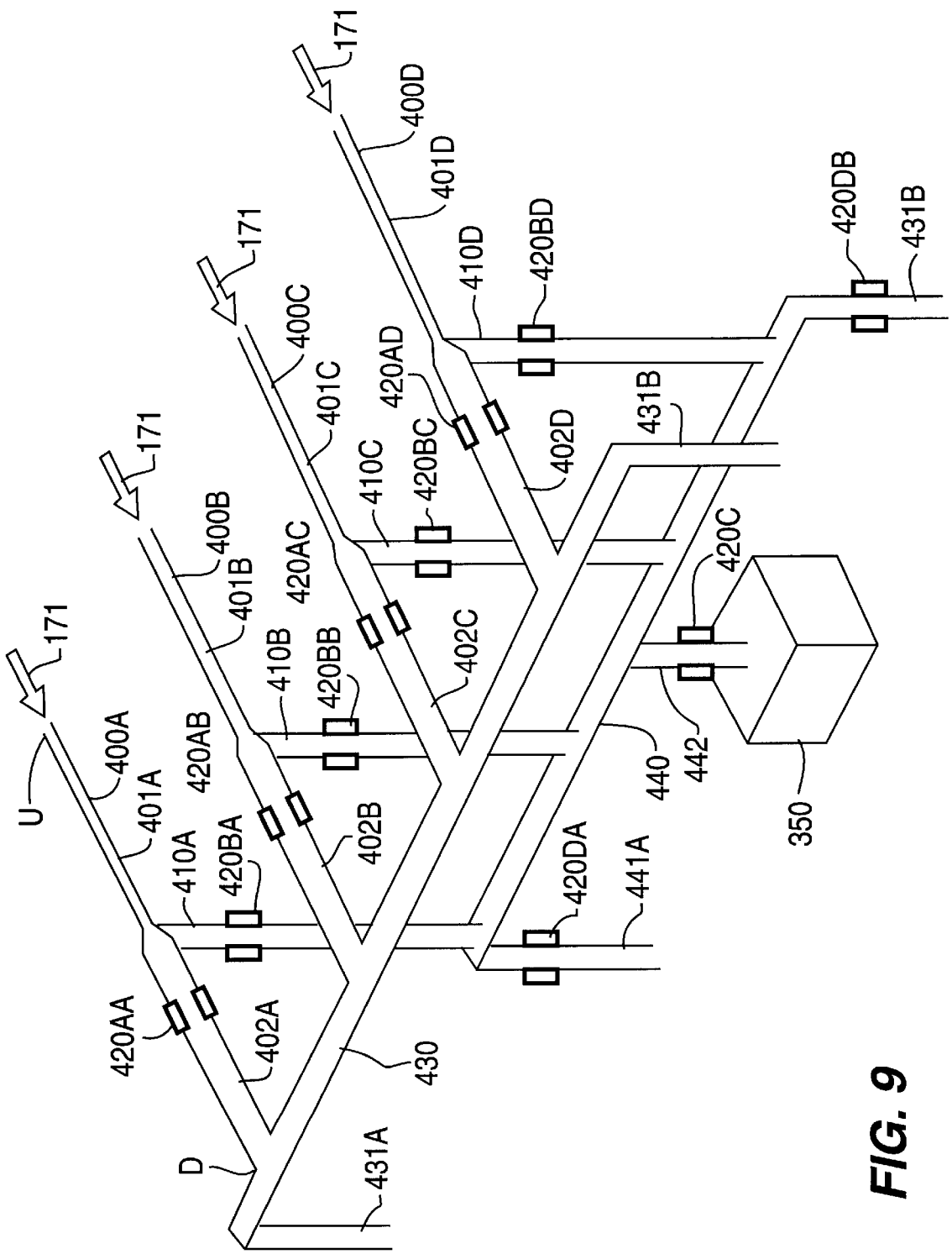
FIG. 9 schematically illustrates a liquid distribution system of the preferential flow liquid distribution system.

Another embodiment of the distribution system wherein a plurality of microscaled reaction cells can be separately addressed by a number of reagent liquids uses a continuous flow system is illustrated schematically in FIG. 9. Features of other distribution systems described in this application can be applied to this embodiment, irrespective of under which subheading they are described.

FIG. 9 illustrates a first continuous flow channel 400A, a second continuous flow channel 400B, a third continuous flow channel 400C and a fourth continuous flow channel 400D, each continuous flow channel having an upstream end U and a downstream end D. Fluid can be pushed through first through fourth continuous flow channels 400A–400D with the assistance of one or more external pumps 171. Third pumps 460 (not shown), which can be electrode-based pumps, can provide further pumping within the first through fourth continuous flow channels 400A–400D. Constricted zones 401A–401D at the upstream end of the first through fourth continuous flow channels 400A–400D have a first cross-sectional area. Open zones 402A–402D at the downstream end of the first through fourth continuous flow channels 400A–400D have a second cross-sectional area that is greater than the first cross-sectional area. At the upstream end of the open zones 402A–402D, are first branch channel 410A, second branch channel 410B, third branch channel 410C and fourth branch channel 410D, respectively. Each of these branch channels 410A–410D preferably has a smaller cross-sectional area than that of the open zones 402A–402D and each flows into a buffer channel 440. In the open zones 402A–402D, there are first alpha constrictor 420AA, second alpha constrictor 420AB, third alpha constrictor 420AC, and fourth alpha constrictor 420AD, respectively.

A constrictor, such as an alpha constrictor, can be a micromachined valve or transducer that is thermally, electromagnetically or pressure actuated, an electrode-based pump operating in flow-blocking mode, or another constrictor recognized in the art. Constrictors operate to reduce flow at a portion of a channel, or, preferably, to shut off flow.

The downstream outlets of the continuous flow channels 400A–400D connect with a common bypass 430 which connects to first drain 431A and second drain 431B.

Branch channels 410A–410C have a first beta constrictor 420BA, second beta constrictor 420BB, third beta constrictor 420BC and fourth beta constrictor 420BD, respectively. From buffer channel 440, there extends a reaction cell conduit 442, a first buffer overflow 441A and a second buffer overflow 441B. Reaction cell conduit 442 has a gamma constrictor 420C. First and second buffer overflows 441A and 441B have first delta constrictor 420DA and second delta constrictor 420DB, respectively.

When a "liquid A" flows through first continuous flow channel 400A and first alpha constrictor 420AA is not in operation, liquid A will tend to flow to the common bypass 430 via the open zone portion of the first continuous flow channel 400A having relatively large cross-sectional area rather than flow through relatively narrow branch channel 410A. First beta constrictor 420BA can be operated to restrict or block flow in branch channel 410A, further assuring greater flow through to the common bypass 430. To direct liquid A to the reaction cell 350, first alpha constrictor 420AA is operated, while first beta constrictor 420BA is not, resulting in greater flow into first branch channel 410A. The entry of liquid A into buffer channel 440 can result in the application of upward pressure at second through fourth branch channels 410B–410D, depending upon the rate of outflow through reaction cell conduit 442 or first or second buffer overflows 441A or 441B. This pressure can be used to inhibit cross contamination with fluids from second, third or fourth continuous flow channels 400B–400D.

All constrictors 420 preferably can operate to stop liquid flow in their respective channels, particularly first through fourth beta constrictors 420BA through 420BD and gamma constrictor 420C.

Figure 10:
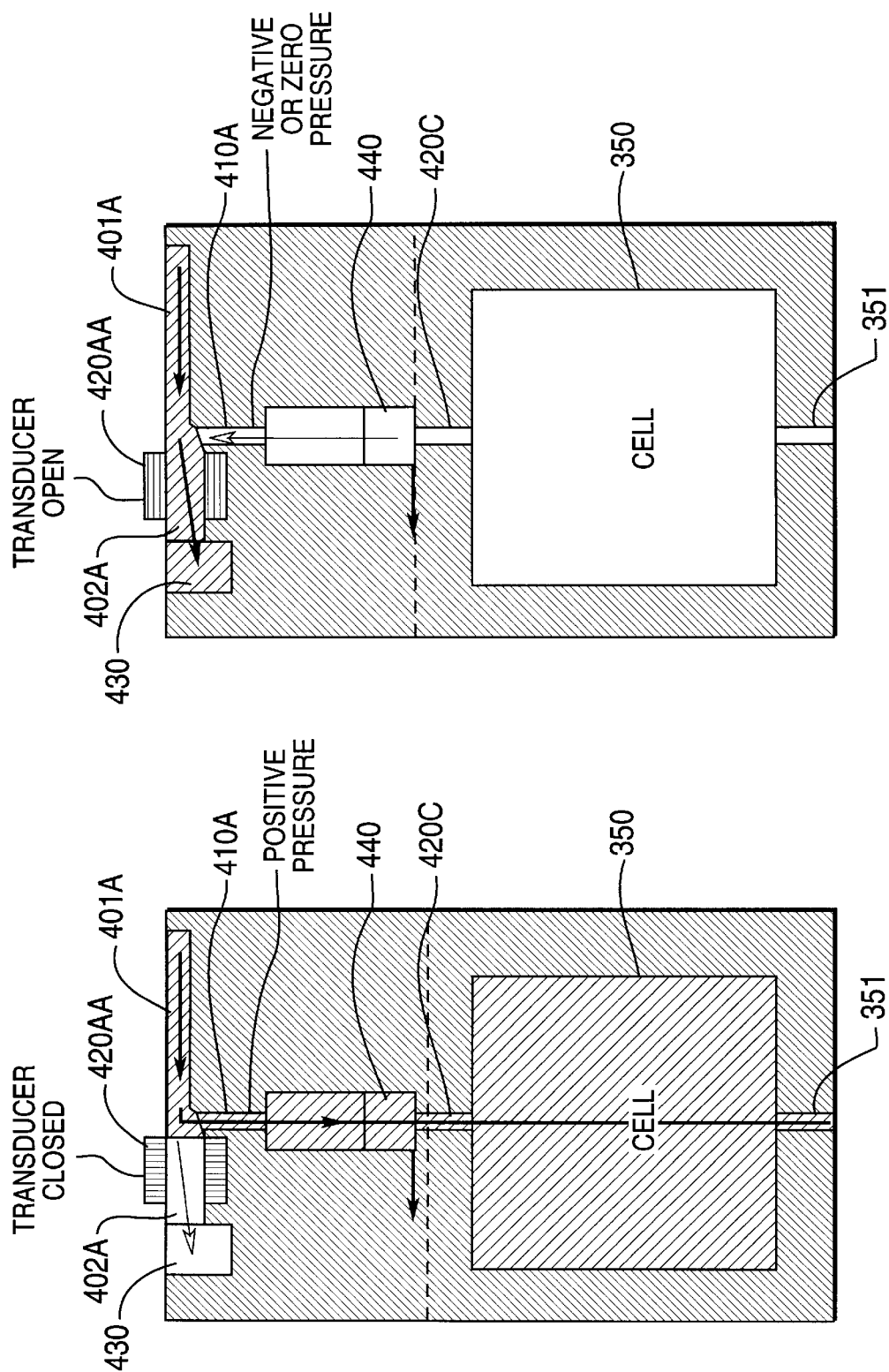
FIGS. 10A and 10B show cross-sectional views of a liquid distribution system of the preferential flow liquid distribution system.

FIG. 10A shows a cross-sectional view of continuous flow channel 400A operated to direct flow into branch channel 410A, while FIG. 10B illustrates the continuous flow channel 400A operated to direct flow into the common bypass 430. A reaction cell 350 and a reaction cell drain 355 are also illustrated.

Figure 11:
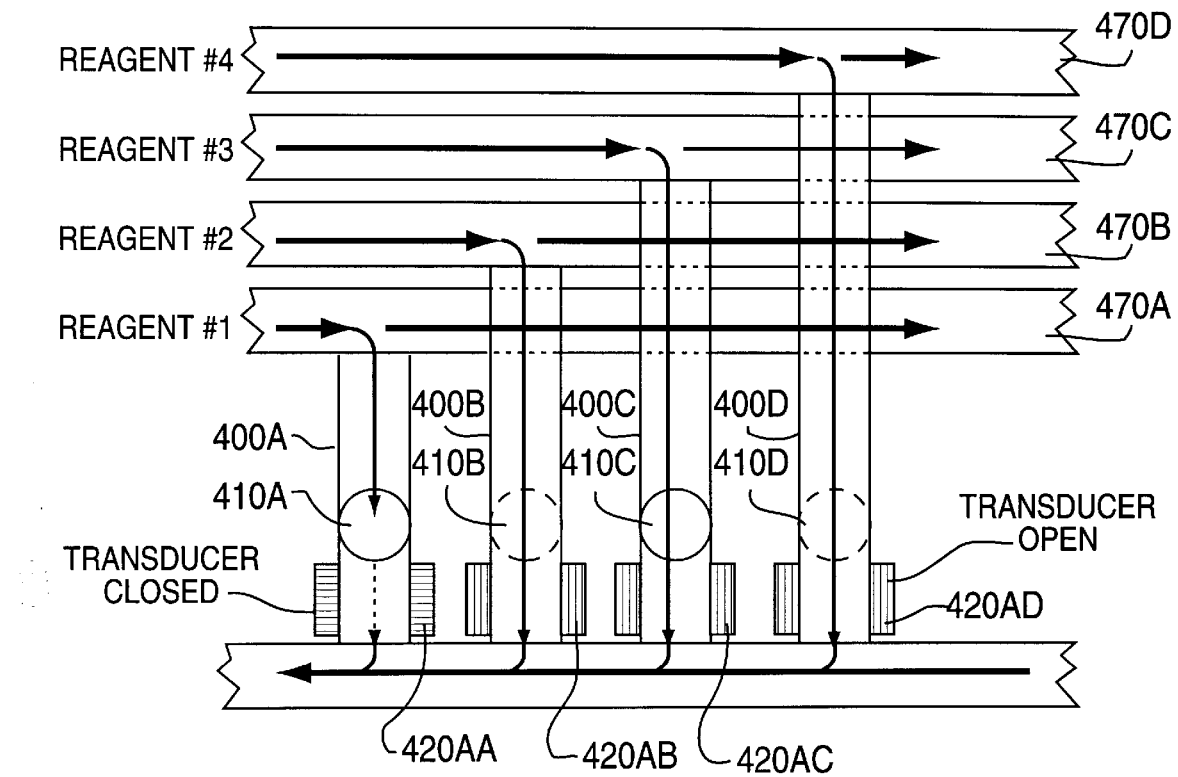
FIG. 11 shows a schematic top view of a liquid distribution system of the preferential flow liquid distribution system.

FIG. 11 shows how the first through fourth continuous flow channels 400A–400D can be connected to a larger grid having first through fourth primary feed channels 470A–470D. First through fourth primary feed channels 470A–470D are located on a higher or lower horizontal plane than first through fourth continuous flow channels 400A–400D, allowing the two sets of channels to be interconnected. In one preferred embodiment, the inlets of each of first through fourth continuous flow channels 400A–400D have third pumps 460 (not illustrated) that facilitate drawing fluid from the first through fourth primary feeder channels 470A–470D.

D. Expansion Valve Liquid Distribution System

The expansion valve liquid distribution system has a reaction cell, two or more feeder channels, a separate conduit connecting each feeder channel to the reaction cell, and a expansion valve for each conduit, wherein the expansion valve has an expanded state that fills a cross-section of the conduit and prevents fluid flow through the conduit and an contracted state that allows fluid flow through the conduit. This embodiment differs from other embodiments in that the distribution system is preferably constructed of plastic, rather than glass or a silicon-based material. Preferred plastics include polyethylene, polypropylene, liquid crystal engineering plastics, polyvinylidine fluoride and polytetrafluoroethylene. Plastics with low moisture vapor transmission rates (e.g., polyethylene, polyvinylidine fluoride and polytetrafluoroethylene) are particularly preferred. Laminates such as a laminate of polyethylene and a polyester such as poly(ethyleneterephthalate) are also preferred for their vapor barrier properties. The channels or conduits of this embodiment are preferably as described below in Section I, which describes fabrication methods. However, this embodiment can more readily be used with larger scale features, such as larger channels and reaction cells. Features of other distribution systems described in this application can be applied to this embodiment, irrespective of under which subheading they are described.

Figure 12:
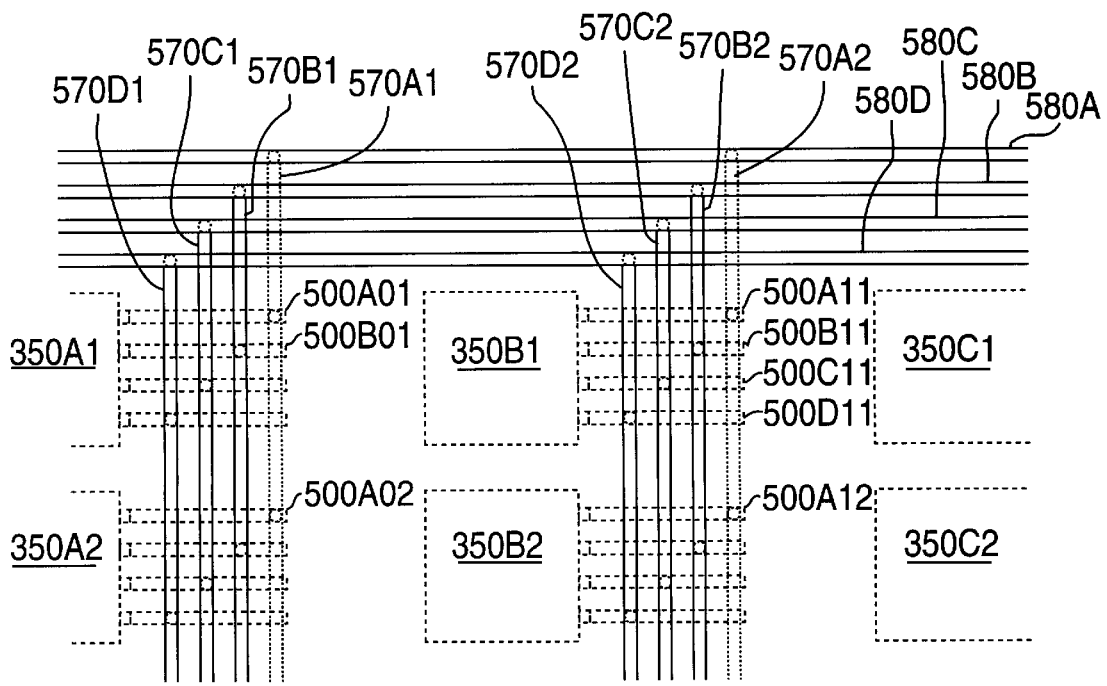
FIG. 12 shows a top view of a liquid distribution system of the expansion valve liquid distribution system.

FIG. 12 shows a schematic having fifth through eighth primary supply channels 580A through 580D, respectively. Fifth primary supply channel 580A connects to first alpha feeder channel 570A1, second alpha feeder channel 570A2, and so on. Sixth through eighth primary supply channels, 580B through 580D, respectively, are also connected to feeder channels. Focusing on second alpha feeder channel 570A2, second beta feeder channel 570B2, second gamma channel 570C2 and second delta feeder channel 570D2, these are each connected to a number of alpha distribution channels 500A, beta distribution channels 500B, gamma distribution channels 500C and delta distribution channels 500D, respectively. For instance, second alpha feeder channel 570A2 is connected to eleventh alpha distribution channel 500A11, twelfth alpha distribution channel 500A12, and so on. Sets of four distribution channels 500, e.g. eleventh alpha distribution channel 500A11, eleventh beta distribution channel 500B11, eleventh gamma distribution channel 500C11, and eleventh delta distribution channel 500D11, are connected to a given reaction cell 350, e.g., reaction cell 350.

As illustrated below, each distribution channel 500 has an expansion valve which can be activated to block flow from the feeder channels 570 into the reaction cell 350 connected via the distribution channel 500. In one preferred embodiment, fluid in the primary supply channels 580 and feeder channels 570 is maintained a constant pressure using upstream pumps and downstream pressure release valves.

Figure 13A:
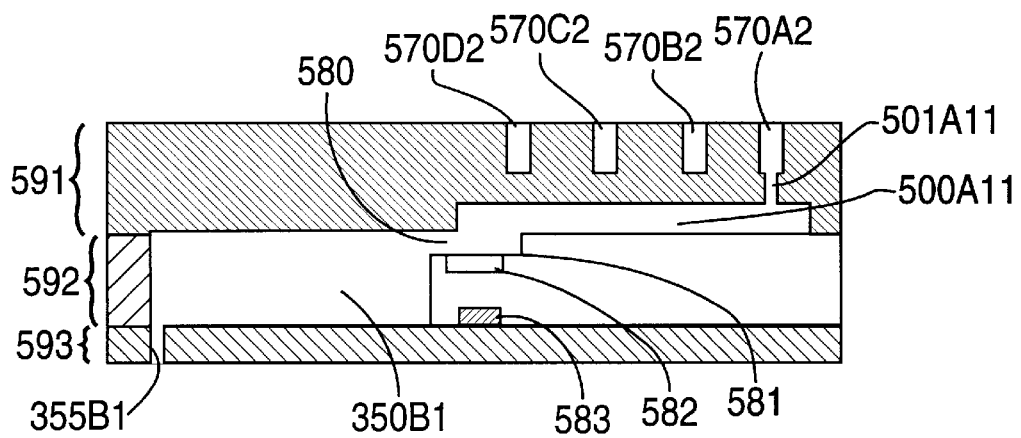
FIGS. 13A–13C show cross-sectional views of various embodiments of the expansion valve liquid distribution system

FIG. 13A shows a cross-section through eleventh alpha distribution channel 500A11. Three of the plates that form the distribution system, first plate 591, second plate 592 and third plate 593, are illustrated. Second alpha feeder channel 570A2, second beta feeder channel 570B2, second gamma feeder channel 570A2 and second delta feeder channel 570 D2 can be formed in a molding process used to form first plate 591. Eleventh alpha distribution channel 500A11 is primarily formed with parts of first plate 591 and second plate 592 and can be formed during the molding process used to form these plates. The portion 501A11 of eleventh alpha distribution channel 500A11 connecting to second alpha feeder channel 570A2 can be formed using a drilling process, such as a laser drilling process. The portion 502A11 (see FIG. 13B) of eleventh alpha distribution channel 500A11 that connects to reaction cell 350B1 is typically formed during the molding of second plate 592. Expansion valve 580 includes a low modulus, elastomeric film 581 such as a hydrocarbon elastomer, acrylonitrile-based elastomer or polyurethane films, which films include natural latex films, ethylene-propylene rubber and acrylonitrile-butadiene-styrene copolymer films. The elastomeric film can, for example, be bonded to the substrate using an adhesive such as a thermal setting acrylic, polyurea or polysulfide adhesive or it can be bonded by thermal compression bonding or ultrasonic welding. Elastomeric film 581 covers a fluid chamber 582 that is filled with a gas, such as air or argon, or with a low-boiling liquid, such as freon or another refrigerant. Situated sufficiently near fluid chamber 582 is an heating element 583, which is preferably controlled by controller 10. The heating element 583 functions to heat the gas or liquid in fluid chamber 582 to cause the expansion of the expansion valve 580. Reaction cell 350B1 has a drain 355B1.

Heating elements 583 can be any number of heating devices known to the art including electrical resistance heaters and infrared light sources, including infrared diode lasers such edge-emitting diode laser arrays available from David Sarnoff Research Center, Princeton, N.J. or the 1300 nm or 1590 nm lasers available from LaserMax Inc., Rochester, N.Y. If the heating element 583 is an infrared light source, the materia that intervenes between the heating element 583 and the fluid chamber 582 preferably transmits at least about 50%, more preferably 80%, of the infrared light from the heating element 583.

Figure 13B:
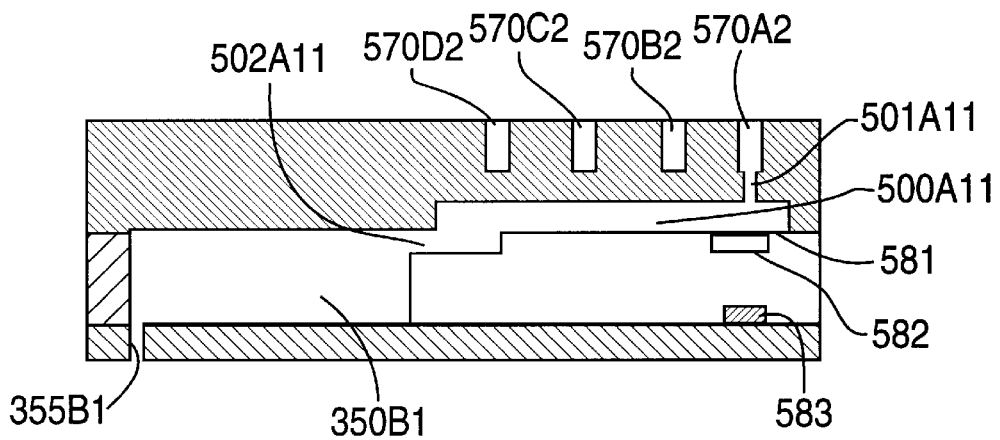

FIG. 13B shows a comparable version of a cut-away view of eleventh alpha distribution channel 500A11 where the expansion valve 580 is positioned differently.

Figure 13C:
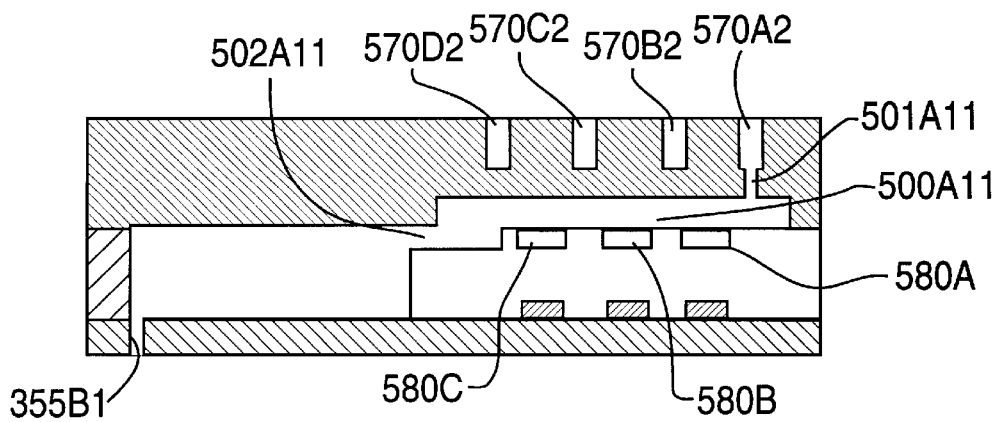

FIG. 13C shows a cut-away of a preferred embodiment where eleventh alpha distribution channel has a first expansion valve 580A, a second expansion valve 580B and a third expansion valve 580C. These three valves can be operated sequentially to create a pumping force that moves liquid into the reaction cell 350B1. For instance, at time one, eleventh distribution channel 500A11 is filled with a liquid and first expansion valve 580A is expanded. At time two, first expansion valve 580A remains expanded and second expansion valve 580C begins to expand, pushing liquid into the reaction cell 350B1. At time three, second expansion valve 580B remains expanded and first expansion valve 580A begins to contract drawing liquid from second alpha feeder channel 570A2 to fill the volume formerly occupied by the expanded valve. Also at time three, third expansion valve 580C begins to expand, forcing liquid to flow into reaction cell 350B1. At time four, third expansion valve 580C remains expanded and second expansion valve 580B begins to contract at the about the same time first expansion valve 580A begins to expand. At time five, first expansion valve 580A is expanded, while the other two expansion valves, 580B and 580C, are contracted, setting the stage for a new pumping cycle.

E. Electrode-based Liquid Distribution System

Figure 14:
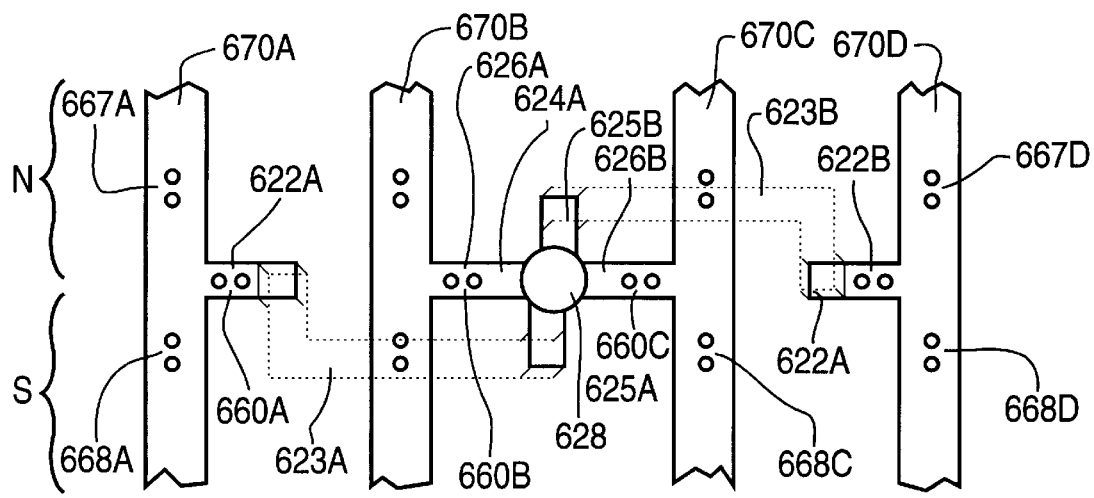
FIG. 14 shows a top view of a portion of an electrode-based liquid distribution system.

FIG. 14 shows a top view of a liquid distribution system of the electrode-based liquid distribution system showing how channels from a number of feeder channels, e.g., alpha through delta feeder channels 670A through 670D, respectively, can connect to a fifth vertical channel 628 that connects to a given reaction cell 350.

In FIG. 14, alpha feeder channel 670A, beta feeder channel 670B, gamma feeder channel 670C and delta feeder channel 670D connect to alpha first distribution channel 622A, alpha second distribution channel 624A, beta second distribution channel 624B, and beta first distribution channel 622B, respectively. Alpha first distribution channel 622A, alpha second distribution channel 624A, beta second distribution channel 624B, and beta first distribution channel 622B have an alpha first electrode-based pump 660A, a beta first electrode-based pump 660B, a gamma first electrode-based pump 660C and a delta first electrode-based pump 660D, respectively. The alpha first distribution channel 622A connects to fifth vertical channel 628 via alpha second connector channel 623A and alpha third connector channel 625A. The beta first distribution channel 622B connects to fifth vertical channel 628 via beta second connector channel 623B and beta third connector channel 625B. Note that alpha second and beta second connector channels 623A and 623B are in a lower plane than their connected alpha first distribution channel 622A and beta first distribution channel 622B, respectively. Alpha second distribution channel 624A and beta second distribution channel 624B each connect directly with fifth vertical channel 628.

Note that the "N" portions (indicated in the figure) of alpha, beta, gamma and delta feeder channels 670A–670D, respectively, are referred to as the "feeder channel inlets", while the "S" portions are referred to as the "feeder channel outlets". The inlets of alpha, beta, gamma and delta feeder channels 670A–670D, have an alpha second electrode-based pump 667A, a beta second electrode-based pump 667B, a gamma second electrode-based pump 667C and a delta second electrode-based pump 667D, respectively. The outlets of alpha, beta, gamma and delta feeder channels 670A–670D, have an alpha third electrode-based pump 668A, a beta third electrode-based pump 668B, a gamma third electrode-based pump 668C and a delta third electrode-based pump 668D, respectively. The voltages used to operate the three electrode-based pumps in the channels that form the three-way junctions (made up of a feeder channel inlet, a feeder channel outlet and a distribution channel) can be adjusted to either allow flow into the distribution channel or to block flow into the distribution channel. Preferably, at each three-way junction, each electrode of the first electrode-based pump 660, second electrode-based pump 667 and third electrode-based pump 668 that is nearest the junction is connected to a common voltage source or ground.

In a preferred embodiment, capillary barriers, for instance located at the four junctions (unnumbered) with fifth vertical channel 628 can be used to limit unintended flow into fifth vertical channel 628. In another preferred embodiment, the alpha and beta first distribution channels 622A and 622B and the alpha and beta second distribution channels 624A and 624B have narrower channel widths that their connected feeder channels 670, so that flow through the distribution channels 622 or 624 is less favored than flow through the feeder channels 670, particularly when the first electrode-based pump 660 in the distribution channels are operated to pump against the unwanted flow. Preferably, one or more of the distribution channels (e.g., alpha first distribution channel 622A) have a channel width at the opening with the three-way junction that is about 50% or less of the width the connected feeder channel 670, more preferably the width is about 40% or less of the width the connected feeder channel 670.

Features of other distribution systems described in this application can be applied to this embodiment, irrespective of under which subheading they are described.

F. Controller

The controller 10 will typically be an electronic processor. However, it can also be a simpler device comprised of timers, switches, solenoids and the like. The important feature of controller 10 is that it directs the activity of the first pumps 360 and second pumps 361 and, optionally, the activity of external pumps 171. A circuit of thin film transistors (not shown) can be formed on the liquid distribution system to provide power to the wells via leads and electrodes, and to connect them with the driving means such as the controller 10, so as to move liquids through the array. Pins can also be formed substrate which are addressable by logic circuits that are connected to the controller 10 for example.

G. Reaction Cells and Reaction Cell Plate

Figure 15A:
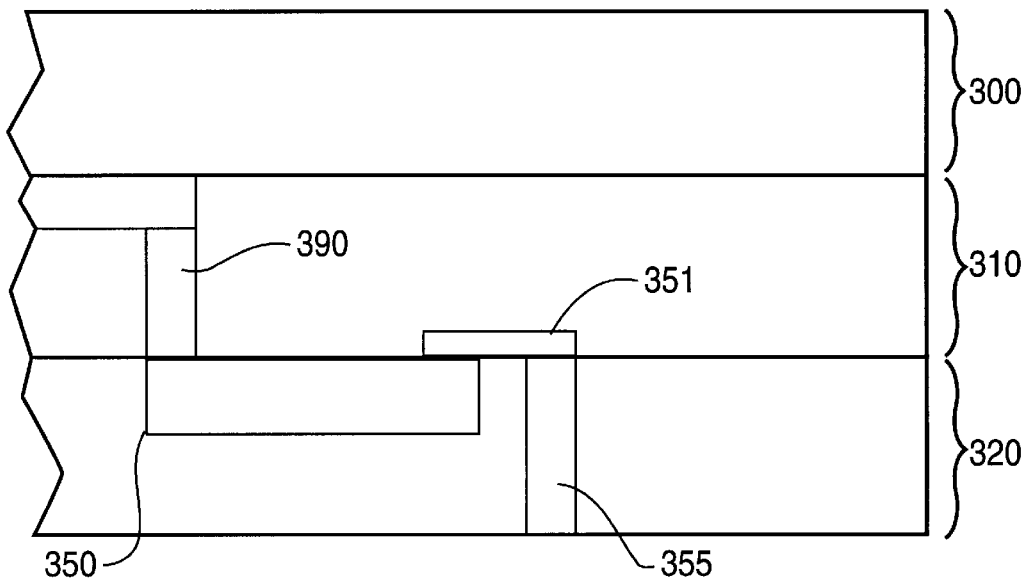
FIGS. 15A and 15B illustrate reaction cell designs.
Figure 15B:
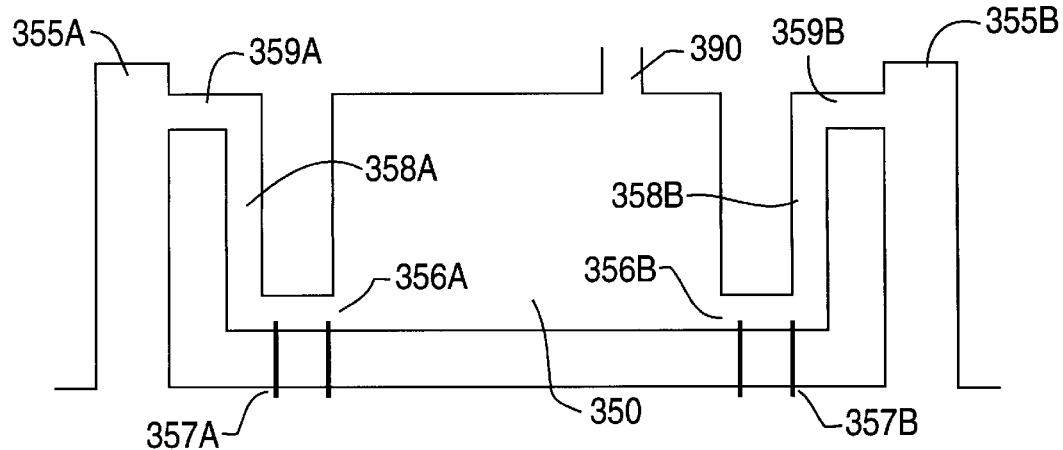

Reaction cells 350 are typically depressions formed in the upper layers of a reaction cell plate 320. The drain 355 to a reaction cell 350 can be open at the bottom of the reaction cell 350, in which case drainage is controlled kinetically and by negative pressure from the connected channels. Alternatively, the drain 355 may be adjacent to the reaction cell 350 and open at a height greater than the height of the floor of the reaction cell 350, as illustrated in FIG. 15A. In FIG. 15A, drain 355 is connected to reaction cell 350 by sluice 351. In this case, flushing volumes, which are substantial volumes relative to the volume of the reaction cell but minuscule in absolute amount, are passed through the reaction cell 350 to remove all of a given reactant previously directed into the reaction cell 350. In another alternative, the reaction cell 350 is connected to a alpha first horizontal drain channel 356A and beta first horizontal drain channel 356B, having an alpha drain pump 357A and beta drain pump 357B, respectively, which can be an electrode-based pumps, as illustrated in FIG. 15B. The alpha and beta first horizontal drain channels 356A and 356B can be connected to alpha vertical drain channel 358A and beta vertical drain channel 358B, which in turn are connected to an alpha and beta second horizontal drain channel 359A and 359B, respectively. Alpha and beta second horizontal drain channel 359A and 359B open into the alpha drain 355A and beta drain 355B. The alpha and beta pumps 357 are operated under the control of the controller 10, which operates the pumps as appropriate to drain the reaction cell 355. Note that this latter drainage structure includes a form of a capillary barrier 370. Where alpha and beta pumps 357A and 357B are electrode-based pumps, one can be operated so that a−flow would drain the reaction cell 350 and the other so that a+flow would drain the reaction cell 350. In this way, no matter what the flow preference of the liquid in the reaction cell 350, one drain mechanism would push fluid out of the reaction cell 350, while the other merely pushed a limited volume of fluid into the reaction cell 350, yielding a net draining effect.

Another way by which the reaction cell 350 can be controllably drained is to use a bottom drain 355 having an outlet channel that has constrictor, such as one of the constrictors described above with reference to the second preferred embodiment.

Drains are optional, since in some uses the amount of liquid moved into a reaction cell 350 is less than the reaction cell's volume. If drains are absent, however, vents are required. Vents for the reaction cells 350 are appropriate in other contexts.

The reaction cell plate can be reversibly bonded to the next higher plate by, for instance, assuring that the two surfaces are smoothly machined and pressing the two plates together. Or, for example, a deformable gasket, such as a teflon, polyethylene or an elastomoric film (such as a natural rubber, ABS rubber, or polyurethane elastomor film) gasket is interposed between the plates. One way to maintain a force adhering the plates against the gasket is to have a number of vacuum holes cut through the bottom plate and the gasket and applying a vacuum at these locations. Generally, the seal should be sufficient so that the pump used to form the vacuum can be shut down after initially forming the vacuum. The gasket is preferably from about 0.0×5 mils to about 1 mil, more preferably from about 0.1 mils to about 0.3 mils in thickness.

Fluid exiting the bottom of the reaction cell plate 320 can, for instance, simply collect in a catch pan or it can diffuse into a porous substrate such a sintered glass, glass wool, or a fabric material. Alternately, a fifth plate 340 is attached to the underside of the reaction cell and has channels that connect the outlets of the reaction cells 350 to individual collection reservoirs from which fluid can be sampled. For instance, the fifth plate 340 is wider than the reaction cell plate 320 and the collection reservoirs are located at the top surface of the fifth plate 340 in the area not covered by the reaction cell plate 320.

Preferably, synthetic processes conducted in the reaction cells 350 of the liquid distribution system will take place on insoluble supports, typically referred to as "beads", such as the styrene-divinylbenzene copolymerizate used by Merrifield when he introduced solid phase peptide synthetic techniques. Merrifield, *J. Am. Chem. Soc.* 85: 2149, 1963. See, also Barany et al., "Recent Advances in Solid-Phase Synthesis," in *Innovation and Perspectives in Solid Phase Synthesis: Peptides, Polypeptides, and Oligonucleotides*, Roger Epton, Ed., collected papers of the 2nd International Symposium, 27–31 Aug. 1991, Canterbury, England, p. 29. These supports are typically derivatized to provide a "handle" to which the first building block of an anticipated product can be reversibly attached. In the peptide synthesis area, suitable supports include a p-alkoyxbenzyl alcohol resin ("Wang" or PAM resin) available from Bachem Bioscience, Inc., King of Prussia, Pa.), substituted 2-chlorotrityl resins available from Advanced Chemtech, Louisville, K.Y., and polyethylene glycol grafted poly styrene resins (PEG-PS resins) are available from PerSeptive Biosystems, Framingham, Mass. or under the tradename TentaGel, from Rapp Polymere, Germany. Similar solid phase supports, such as polystyrene beads, are also used in the synthesis of oligonucleotides by the phosphotriester approach (see Dhristodoulou, "Oligonucleotide Synthesis: Phosphotriester Approach," in *Protocols for Oligonucleotide Conjugates*, S. Agrawal, Ed., Humana Press, N.J., 1994), by the phosphoramidite approach (see Beaucage, "Oligodeoxynucleotide Synthesis: Phosphoramidite Approach," in *Protocols for Oligonucleotide Conjugates*, S. Agrawal, Ed., Humana Press, N.J., 1994), by the H-phosponate approach (see Froehler, Oligodeoxynucleotide Synthesis: H-Posponate Approach," in *Protocols for Oligonucleotide Conjugates*, S. Agrawal, Ed., Humana Press, N.J., 1994), or by the silyl-phosphoramidite method (see Damha and Ogilvie, Oligodeoxynucleotide Synthesis: "Silyl-Phosphoramidite Method," in *Protocols for Oligonucleotide Conjugates*, S. Agrawal, Ed., Humana Press, N.J., 1994). Suitable supports for oligonucleotide synthesis include the controlled pore glass (cpg) and polystyrene supports available from Applied Biosystems, Foster City, Calif. Solid supports are also used in other small molecule and polymeric organic syntheses, as illustrated in oligocarbamate synthesis for organic polymeric diversity as described by Gorden et al., *J. Medicinal Chem.* 37: 1385–1401, 1994.

Preferably, the reaction cells 350 are rectangular with horizontal dimensions of about 400 microns to about 1200 microns, more preferably about 500 microns to about 1000 microns, yet more preferably about 640 microns, and a depth of about 200 microns to about 400 microns. Where beads will be used in the reaction cells 350, the depth of the reaction cells 350 is preferably at least about 50 microns greater than the swelled diameter of the beads. The support beads typically used as in solid-phase syntheses typically have diameters between about 50 microns and about 250 microns, and reactive site capacities of between about 0.1 mmoles/g and about 1.6 mmoles/g. Typically, between about 1 and about 10 of such beads are loaded into a reaction cell 350 to provide a desired capacity of between about 1 nmole and about 10 nmole per reaction cell 350. Recently, beads have become available that have a diameter that ranges between about 200 microns and about 400 microns, depending on the solvent used to swell the beads and the variation in size between the individual beads, and a reactive site capacity of between about 5 nmole and about 20 nmole per bead have become available. These large beads include the beads sold by Polymer Laboratories, Amhearst, Mass. Desirable reactive site functionalities include halogen, alcohol, amine and carboxylic acid groups. With these large beads, preferably only one bead is loaded into each reaction cell 350.

Another option for creating a solid support is to directly derivatize the bottom of the reaction cell 350 so that it can be reversibly coupled to the first building block of the compound sought to be synthesized. The chemistry used to do this can be the same or similar to that used to derivatize controlled pore glass (cpg) beads and polymer beads. Typically, the first step in this process is to create hydroxyl groups (if they do not already exist on the support) or amino groups on the support. If hydroxyl groups exist or are created, they are typically converted to amino groups, for instance by reacting them with gamma-aminopropyl triethoxy silane. Flexible tethers can be added to the amino groups with cyclic acid anhydrides, reactions with polymerized alkylene oxides and other methods known to the art. Examples of such methods are described in Fields et al., "Synthetic Peptides: A User's Guide," W. H. Freeman and Co., Salt Lake City, Utah, 1991.

Methods of creating reactive sites include, for the case where the reaction cell plate 320 is made of plastic, exposing the bottom of the reaction cells 350 to a reactive plasma, such as that created by a glow-discharge in the presence of ammonia or water, to create $NH_2$ groups. Such procedures are described in "Modification of Polymers," Carraher and Tsuda, eds., American Chem. Soc., Washington, D.C., 1980. Another method, useful with glass, ceramic or polymeric substrates, is depositing a film of silicon monoxide by vapor deposition at low temperature to create hydroxyl functionalities. Glass surfaces can be treated with alkali, for instance with KOH or NaOH solutions in water or water/alcohol mixtures, to expose hydroxyl functional groups. Non-annealed borosilicate glass surfaces, including coatings of non-annealed borosilicate glass created by chemical vapor deposition, can be etched, for instance with hydrofluoric acid dissolved in water, to dissolve the regions that are rich in boron, which process creates a porous structure with a large surface area. This porous structure can be treated with alkali to expose hydroxyl groups. The degree of reactive site substitution on such surfaces is preferably at least about 83 nmoles per $cm^2$, more preferably at least about 124 nmoles per $cm^2$ (implying a substitution in 500 micron by 500 micron reaction cell 350 of at least about 0.31 nmole), yet more preferably at least about 256 nmoles per $cm^2$.

The above described methods for using the bottom of the reaction cells 350 as a solid support can be supplemented by methods that increase the surface area of the bottom of the reaction cells 350. One method is to create columnar structures of silicon monoxide, for instance by thermal evaporation of $SiO_x$. Another such method is to insert into the reaction cells fabrics, such as non-woven glass or plastic (preferably fiberglass or polypropylene fiber) fabrics and plasma treating the fabric to create reactive sites.

Another method uses spin-on glass, which creates a thin film of nearly stoichiometric $SiO_2$ from a sil-sesquioxane ladder polymer structure by thermal oxidation. Sol-gel processing creates thin films of glass-like composition from organometallic starting materials by first forming a polymeric organometallic structure in mixed alcohol plus water and then careful drying and baking. When the sol-gel system is dried above the critical temperature and pressure of the solution, an aerogel results. Aerogels have chemical compositions that are similar to glasses (e.g. $SiO_2$) but have extremely porous microstructures. Their densities are comparably low, in some cases having only about one to about three percent solid composition, the balance being air.

H. Capillary barriers

Capillary barriers have been described above with reference to FIGS. 4A and 4B. However, more complex design considerations than were discussed above can, in some cases, affect the design of the capillary barrier. In some cases it is desirable to narrow the sluice formed by second opening 362 or third opening 363 to increase the impedance to flow (i.e., the frictional resistance to flow) as appropriate to arrive at an appropriate flow rate when the associated first pump 360 or second pump 361 is activated. Such a narrowing is illustrated by comparing the sluice of FIG. 16A with the narrowed sluice of FIG. 16D. The problem that this design alteration can create is that narrower channels can increase capillary forces, thereby limiting the effectiveness of channel breaks.

Figure 16D:
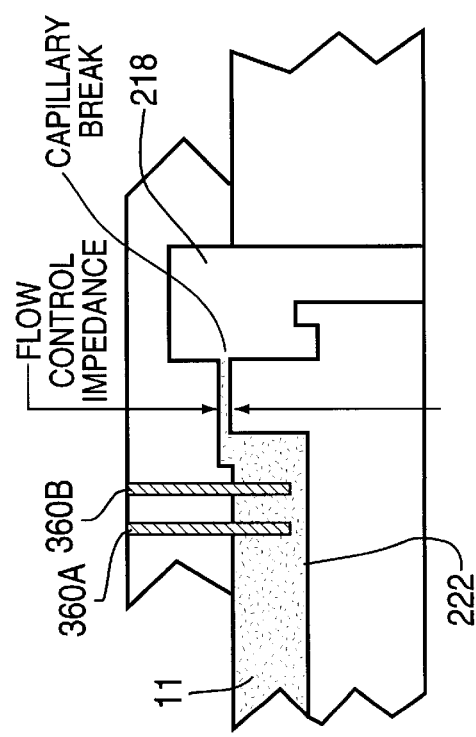
FIGS. 16A–16D show various capillary barrier designs.
Figure 16C:
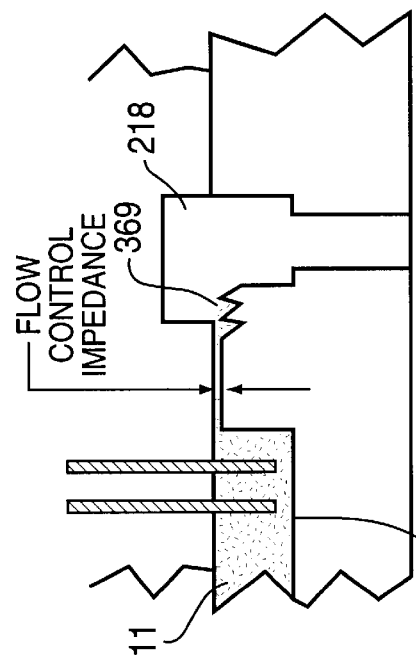
Figure 16A:
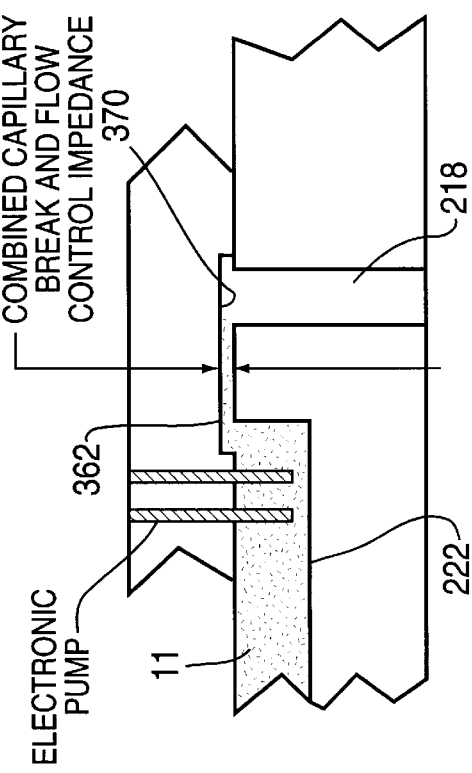
Figure 16B:
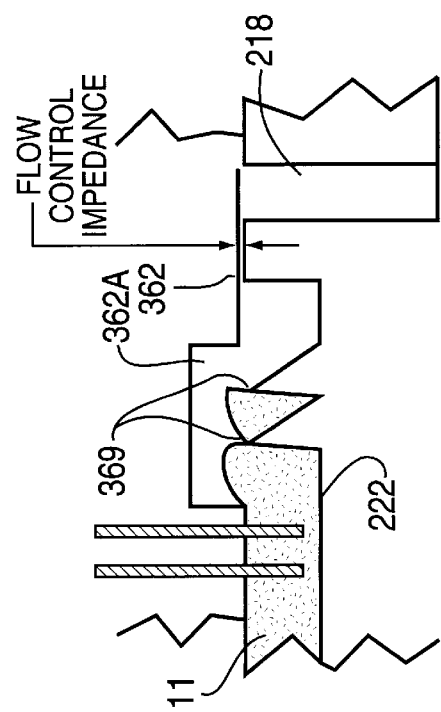

Thus, in one preferred embodiment, a channel break further includes one or more upwardly oriented sharp edges 369, as illustrated in FIGS. 16B and 16C. More preferably, a channel break includes two or more upwardly oriented sharp edges 369. In FIG. 16B, portion 362A of opening 362 is cut more deeply into first plate 300 to create an open space useful for the operation of upwardly oriented sharp edges 369.

I. Fabrication of Plates, Channels, Reservoirs and Reaction Cells

The liquid distribution systems of the invention can be constructed a support material that is, or can be made, resistant to the chemicals sought to be used in the chemical processes to be conducted in the device. For all of the above-described embodiments, the preferred support material will be one that has shown itself susceptible to microfabrication methods that can form channels having cross-sectional dimensions between about 50 microns and about 250 microns, such as glass, fused silica, quartz, silicon wafer or suitable plastics. Glass, quartz, silicon and plastic support materials are preferably surface treated with a suitable treatment reagent such as a siliconizing agent, which minimize the reactive sites on the material, including reactive sites that bind to biological molecules such as proteins or nucleic acids. As discussed earlier, the expansion valve liquid distribution system is preferably constructed of a plastic. In embodiments that require relatively densely packed electrical devices, a non-conducting support material, such as a suitable glass, is preferred. Corning borosilicate glass, and Corning 7740 borosilicate glass, available from Corning Glass Co., Corning, N.Y., are among the preferred glasses.

The liquid distribution system of the invention is preferably constructed from separate plates of materials on which channels, reservoirs and reaction cells are formed, and these plates are later joined to form the liquid distribution system. This aspect of the invention is described in some detail with respect to the hydrologic liquid distribution system. Preferably, the reaction cell plate, e.g. reaction cell plate 320, is the bottom plate and is reversibly joined to the next plate in the stack. The other plates forming the distribution system, which preferably comprise two to three plates are preferably permanently joined. This joinder can be done, for instance, using adhesives, or techniques such as glass-glass thermal bonding.

One preferred method of permanently joining the plates is to first coat the plate with a layer of glass glaze generally having a thickness between about 50 microns and about 500 microns, more preferably between about 75 microns and about 125 microns. The above thicknesses contemplate that substantial amounts of channel structure will be formed in the glaze layer. Otherwise, the glaze generally has a thickness between about 1 microns and about 100 microns, more preferably between about 10 microns and about 25 microns. These methods are preferably applied to join glass plates. Suitable glazes are available from Ferro Corp., Cincinnati, Ohio. The glazed plate is treated to create channels, reservoirs, or reaction cells as described below. The glazed plate is positioned against another plate, which preferably is not glazed, and the two plates are heated to a temperature of about the softening temperature of the glaze or higher, but less than the softening temperature for the non-glaze portion of the plates.

Another preferred method of permanently joining glass plates uses a field assisted thermal bonding process. It has now been discovered that glass-glass sealing using field assist thermal bonding is possible despite the low conductivity of glass if a field assist bonding material is interposed between the plates to be bonded.

To the top or bottom surface of one glass plate a layer of a field assist bonding material is applied. Preferably, the field assist bonding material layer has a thickness between about 50 nm and about 1,000 nm, more preferably, between about 150 nm and about 500 nm. The field assist bonding material can be a material capable of bonding glass substrates using the method described herein. Preferably, the field assist bonding material is silicon or silica. More preferably, the field assist bonding material is silicon.

Figure 17:
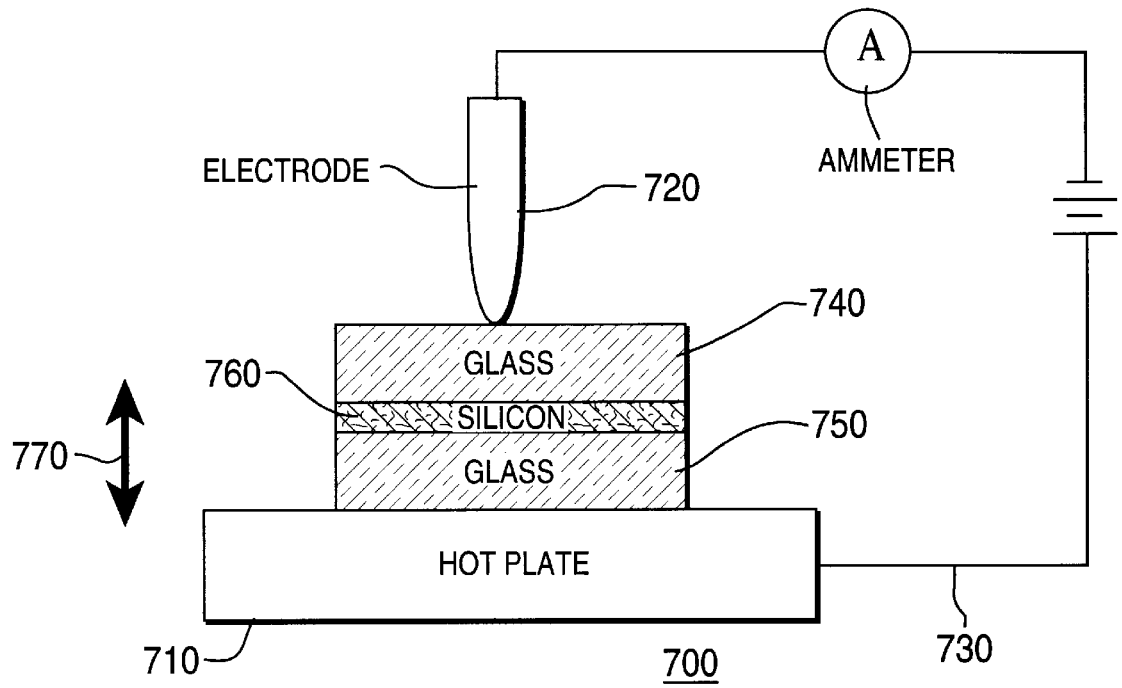
FIG. 17 shows a device for conducting field assisted bonding of plates.

The field assist bonding material can be applied to a plate, for instance, by chemical vapor deposition or by a sputtering process where surface molecules are emitted from a cathode when the cathode is bombarded with positive ions from a rare gas discharge and the surface molecules collide with and bond to a nearby substrate. Pursuant to the present invention, silicon layers of between about 150 nm and about 500 nm thickness have been bonded to glass plates under conditions that can be expected to generate an outer surface layer of silicon dioxide, such as an about 20 Å layer, although the sealing process is believed to be effective in the absence of this layer. The coated plate is treated, as needed, to create channels, reservoirs, or reaction cells using the method described below. Alternatively, the plate was so treated prior to coating with the field-assist bonding material. The coated plate is then positioned against another plate, which preferably is not coated, and placed in a field assisted bonding device 700 such as that illustrated in FIG. 17. The field assisted bonding device 700 has a heating device 710, such as a heating plate. The field assisted bonding device 700 further has an electrode 720 and a ground 730 that allows a voltage to be applied across the first plate 740 and the second plate 750, to which has been applied a layer of silicon 760. Arrows 770 indicate the electric field orientation. Generally, the field assisted bonding is conducted under a normal atmosphere.

The plates are brought to a temperature that is effective, when an appropriate electric field is applied across the plates, to accelerate the bonding process. While not wishing to be bound by theory, it is believed that the combination of a cathode applied to the first glass plate 740 and the greater exchange-site mobility of ions (such as sodium ions) caused by the elevated temperature causes an ion depletion on the face of the first glass plate 740 opposite that to which the cathode is applied. The ion depletion, it is believed, causes a surface charge at the bottom surface of first glass substrate 740, which correlates with the creation of a strong localized electrostatic attraction for the second substrate 750. It is clear that this process creates strong bonding between the substrates and, it is believed that this is due to the formation of chemical bonds between the silica of the first glass substrate 740 and the silicon coated onto the second glass substrate 750. Preferably, the temperature is brought to from about 200° C. to about 600° C., more preferably from about 300° C. to about 450° C. During the process an voltage typically from about 200 V to about 2,500 V, preferably from about 500 V to about 1500 V, is applied across the first glass plate 740 and second glass plate 750. The voltage most suitably applied varies with the thickness of the glass plates. The voltage pulls the first glass plate 740 and second glass plate 750, including the silicon layer 760 applied to one of the plates, into intimate contact. Typically, hermetic sealing is achieved within minutes to about an hour, depending on the planar dimensions of the glass plates. The time required to achieve adequate sealing varies with, among other things, the smoothness of the plates, the electrical field strength, the temperature, and the dimensions of the plates. Bonding between the plates is typically apparent visually, since it is accompanied by the disappearance of the interface between the plates and the formation of gray color at the bonded regions that can be seen when an observer looks through the thinner dimensions of the two plates.

The method described above can be used to bond a glass substrate to another glass substrate and to a third glass substrate simultaneously.

Those of ordinary skill will recognize that while a hot plate is illustrated as providing the heating for the thermal assisted bonding, other heating devices, including ovens, may be used. It will also be realized that it is desirable to match, when possible, the coefficients of thermal expansion of the substrates to be bonded.

The reservoirs, reaction cells, horizontal channels and other structures of the fluid distribution system can be made by the following procedure. A plate, that will for instance make up one of feedthrough plate 300, distribution plate 310, reaction cell plate 320 or intermediate plate 330, is coated sequentially on both sides with, first, a thin chromium layer of about 500 Å thickness and, second, a gold film about 2000 angstroms thick in known manner, as by evaporation or sputtering, to protect the plate from subsequent etchants. A two micron layer of a photoresist, such as Dynakem EPA of Hoechst-Celanese Corp., Bridgewater, N.J., is spun on and the photoresist is exposed, either using a mask or using square or rectangular images, suitably using the MRS 4500 panel stepper available from MRS Technology, Inc., Acton, Mass. After development to form openings in the resist layer, and baking the resist to remove the solvent, the gold layer in the openings is etched away using a standard etch of 4 grams of potassium iodide and 1 gram of iodine ($I_2$) in 25 ml of water. The underlying chromium layer is then separately etched using an acid chromium etch, such as KTI Chrome Etch of KTI Chemicals, Inc., Sunnyvale, Calif. The plate is then etched in an ultrasonic bath of $HF$—$HNO_3$—$H_2O$ in a ratio by volume of 14:20:66. The use of this etchant in an ultrasonic bath produces vertical sidewalls for the various structures. Etching is continued until the desired etch depth is obtained. Vertical channels are typically formed by laser ablation.

The various horizontal channels of the distribution system embodiments typically have depths of about 50 microns to about 250 microns, preferably from about 50 microns to about 100 microns, more preferably from about 50 microns to about 80 microns. The widths of the horizontal channels and the diameters of the vertical channels are typically from about 50 microns to about 200 microns, preferably from about 100 microns to about 200 microns, more preferably from about 120 microns to about 150 microns.

J. Fabrication of Electrode-Based Pumps

In many embodiments, the liquid distribution systems of the invention require the formation of numerous electrodes for pumping fluids through the liquid distribution system. These electrodes are generally fabricated in the top glass plate of the liquid distribution system. Typically each pair of electrodes is closely spaced (e.g. 50 to 250 microns separation). The electrodes are fabricated with diameters of preferably about 25 microns to about 150 microns, more preferably about 50 microns to about 75 microns. In preferred embodiments, the liquid distribution system has 10,000 reaction cell 350 with each reaction cell 350 having 6–10 associated electrode-based pumps. Thus, a liquid distribution system can require about 200,000 to about 300,000 electrodes. To produce such structures using mass production techniques requires forming the electrodes in a parallel, rather than sequential fashion. A preferred method of forming the electrodes involves forming the holes in the plate (e.g., feedthrough plate 300) through which the electrodes will protrude, filling the holes with a metallic thick film ink (i.e., a so-called "via ink", which is a fluid material that sinters at a given temperature to form a mass that, upon cooling below the sintering temperature, is an electrically conductive solid) and then firing the plate and ink fill to convert the ink into a good conductor that also seals the holes against fluid leakage. The method also creates portions of the electrodes that protrude through the plate to, on one side, provide the electrodes that will protrude into the liquids in fluid channels and, on the other side, provide contact points for attaching electrical controls.

For example, holes are drilled in 500 micron thick plates of borosilicate glass using an excimer laser. Holes having diameters between 50 and 150 microns are then filled with thick film inks, using an commercial Injection Via-fill Machine (Pacific Trinetics Model #VF-1000, San Marcos, Calif.). It has been unexpectedly discovered that only select formulations of via inks sufficiently function to fill such high aspect ratio holes such that the fired ink adheres to the sides of the holes, does not crack during the firing process, and seals the holes against fluid flow. One parameter that is important to so forming sealed, conductive conduits through high aspect holes is selecting metal powder and glass powder components for the via ink that have sufficiently fine dimensions. One suitable formulation uses: 12-507 Au powder (Technic Inc., Woonsocket, R.I.), 89.3% w/w; F-92 glass (O. Hommel Co., Carnegie, Pa.), 5.7% w/w; 15% w/v ethyl cellulose N-300 (N-300, Aqualon, Wilmington, Del.) in Texanol™ (monoisobutarate ester of 2,2,4-trimethyl-1,3-pentandiol, Eastman Chemical Products, Kingsport, Tenn.), 2.4% w/w; 15% w/v Elvacite 2045™ (polyisobutyl methacrylate) in Terpineol T-318 (mixed tertiary terpene alcohols, Hercules Inc., Wilmington, Del.), 2.1% w/w; and Duomeen TDO™ (N-tallow alkyl trimethylenediamine oleates, Akzo Chemicals, Chicago, Ill.), 0.5% w/w. The gold powder from Technic, Inc. has an average particle diameter of 0.9 microns. Another suitable formulation uses: Ag Powder Q powder (Metz, South Plainfield, N.J.), 80.8% w/w; F-92 glass (O. Hommel Co. Carnegie, Pa.), 5.2% w/w; VC-1 resin (37% w/w Terpineol T-318, 55.5% w/w butyl carbitol, 7.5% w/w ethylcellulose N-300, Aqualon, Wilmington, Del.), 3.7 % w/w; 15% w/v ethyl cellulose N-300 in Texanol™, 4.0% w/w; 15% W/V Elvacite 2045™ (polyisobutyl methacrylate) in Terpineol T-318, 4.1% w/w; Duomeen TDO™, 0.6% w/w; and Terpineol, 1.6% w/w. These formulations were fired at 550° C. to form high aspect ratio conductive conduits.

When the size of the glass or metal powders increases, good filling properties (lack of cracking, good sealing against liquids, good adherence to sides of hole) can often still be obtained by decreasing the amount of organic in the via ink.

The devices used to insert via inks into holes in a plate typically include a metal stencil with openings corresponding to the openings in the plate. Via ink is applied above the stencil, which rests on the plate, and a bladder device is used to pressurize the ink to force it to fill the holes. After filling, the plate with its via ink-filled holes is removed for further processing, as described below.

Prior to firing, much of the organic component is evaporated away by, for example, placing the ink-filled plate in a oven (e.g. at 100° C.) for one to five minutes. Preferably, the firing is conducted at a temperature from about 450° C. to about 700° C., more preferably from about 500° C. to about 550° C. However, the upper end of the appropriate firing temperature range is primarily dictated by the temperature at which the plate being treated would begin to warp. Accordingly, with some types of plates much higher temperatures could be contemplated.

To assure that there is conductive material that protrudes above and below the glass plate after firing, the top and bottom surface of the plate can be coated with a sacrificial layer of thicknesses equaling the length of the desired protrusions. The sacrificial layers can be applied before or after the holes are formed in the plate. If before, then the holes are formed through both the glass plate and the sacrificial layers. If after, then (a) corresponding openings through the sacrificial layers can be created by creating a gas pressure difference from one side of the plate to the other, which pressure difference blows clear the sacrificial material covering the holes or (b) such openings through at least the top sacrificial layer are created when the pressure of the ink pushes through the sacrificial layer and into the holes (leaving an innocuous amount of sacrificial layer material in the holes). An appropriate sacrificial layer burns away during the firing process. Sacrificial layers can be made coating a plate with, for instance, 5–25 w/w % mixtures of ethyl cellulose resin (e.g., Ethyl Cellulose N-300, Aqualon, Wilmington, Del.) dissolved in Terpineol T-318™ or Texanol™, or 5–50% w/w mixtures of Elvacite 2045™ in Terpineol T-318™. After firing, the surfaces of the electrode can be enhanced plating metals, such as nickel, silver, gold, platinum, rhodium, etc. The depositions can be performed using standard electrolytic and/or electroless plating baths and techniques.

Preferably, where a plate that is to contain etched openings will be processed to include electrodes, the etching occurs first, followed by coating with the sacrificial layer and forming the electrode holes.

In an alternate method of manufacture, for each pump, two or more metal wires, for example gold or platinum wires about 1–10 mils in diameter, are inserted into the openings in the channel walls about, e.g., 150 microns apart. The wires were sealed into the channels by means of a conventional gold or platinum via fill ink made of finely divided metal particles in a glass matrix. After applying the via fill ink about the base of the wire on the outside of the opening, the channel is heated to a temperature above the flow temperature of the via fill ink glass, providing an excellent seal between the wires and the channel. The via ink, which is used to seal the holes, can be substituted with, for instance, solder or an adhesive.

I. Miscellaneous Features

In the case where the temperature of a particular well is to be monitored or changed, a means of heating or cooling the well is built into the well, as will be further explained below with reference to FIG. 20. The first well 36 in this example has deposited on its bottom surface a thin film 57 of a suitable metal oxide, such as tin oxide or indium tin oxide. The thin film 57 is connected by means of an electrically conductive metal connection 58 to the end or outer edge of the well 36. The tin oxide coating 57 serves as a heater element for the well 36. The sides of the well 36 have a surface bimetal film 59 and leads 60, suitably made of chromel-alumel alloys, forming a thermocouple to measure the temperature in the well when a source of current is applied to the tin oxide coating 57 and to the leads 58. A voltage applied to the well 36 via electrodes 56 deposited on the backside as shown regulates the temperature in the well. The amount of current applied can be regulated by the controller 10 in response to the temperature measured through the leads 60.

In some applications of the liquid distribution system a significant vapor pressure may develop in reaction cell 350, causing a back pressure into the distribution plate 310. Thus preformed valves 70 (see FIG. 21A) formed of bimetallic materials as described by Jerman et al, "Understanding Microvalve Technology", Sensors, September 1994 pp 26–36 can be situated in third vertical channel 390. These materials have a thermal expansion mismatch. When the temperature in the reaction cell 350 is low, the ball valve 62 is in its normal position permitting free flow of fluids into the well 36 (see FIG. 21 A). As the temperature in the well 36 increases, the ball valve 62 moves to a cooler position (FIG. 21B) blocking the third vertical channel 390 to isolate the reaction cell 350, thereby preventing fluids from passing into and out of the first well 36. Alternatively, a conventional check valve having a bearing, such as a bearing made of quartz or polytetrafluoroethylene polymer can be used to isolate the reaction cell 350. Where it is important to have the capability to have fluid flow counter to the direction established by the check valve, the check valve can have an insulating or magnetic bearing, which can be moved to allow such counterflow with externally applied electrostatic-or magnetic fields.

Other features of liquid distribution systems are described in of U.S. application Ser. No. 08/338,703, titled "A Partitioned Microelectronic and Fluidic Device Array for Clinical Diagnostics and Chemical Synthesis," filed Nov. 10, 1994, now U.S. Pat. No. 5,585,069; U.S. application Ser. No. 08/469,238, titled "Apparatus and Methods for Controlling Fluid Flow in Microchannels," filed Jun. 6, 1995, now U.S. Pat. No. 5,632,876; and U.S. application Ser. No. 08/483,331, titled "Method and System for Inhibiting Cross-Contamination in Fluids of Combinatorial Chemistry Device," filed Jun. 7, 1995, now U.S. Pat. No. 5,603,351. The disclosure of patent documents recited in this paragraph are incorporated herein by reference in its entirety.

EXAMPLES

Example 1—Liquids Dumped with a simple electrode-based pump

Using the 1 mm capillary with a two electrode-pump described above in Section B.ii., a number liquids have been tested, including the following solvents:

| Solvent | Flow direction | voltage applied |
| --- | --- | --- |
| N-methyl-pyrrolidinone (NMP) | + | 1470 |
| Dimethyl formamide (DMF) | + | 390 |
| Dichloromethane (DCM) | − | 686 |
| Methanol (MeOH) | − | 489 |
| Isopropanol (IPA) | + | |
| Acetone | + | |
| Acetonitrile | + | |

The following solutions in NMP, at 0.1M unless otherwise indicated, have been tested:

| Reagent | Flow direction |
| --- | --- |
| trans-4-(trifluoromethyl)-cinnamic acid | − |
| 5-benzimidazolecarboxylic acid | − |
| N,N-dicyclohexylcarbodiimide | + |
| isobutylamine | + |
| 2-(1H-benzotriazole-1-yl)-1,1,3,3-tetramethyluronium hexafluorophosphate (HBTU) | No flow at 0.1M, flow occurs lower concentrations (0.01–0.1M) |

The following solutions in DMF, all at 0.1M excepting piperidine, which was 20% v/v, have been tested:

| Reagent | Flow direction* |
| --- | --- |
| p-carboxybenzenesulfonamide | −P |
| 4-fluorophenylacetic acid | −P |
| 4-methoxyphenylacetic acid | −P |
| m-trifluoromethylbenzoic acid | −P |
| 3-(4-methoxyphenyl)propionic acid | − |
| 4-bromocinnamic acid | −P |
| terephthalic acid | −P |
| isophthalic acid | −P |
| 1,3-phenylenediacetic acid | −P |
| 1,4-phenylenediacetic acid | −P |
| 3-(4-carboxyphenyl) propionic acid | −P |
| 1,4-phenyl(enedipropionic acid | −P |
| 4,4'-oxybis (benzoic acid) | −P |
| 4,4'-dicarboxybenzophenone | −P |
| piperidine | + |
| 1,3-diisopropylcarbodiimide | + |
| allylamine | + |
| butylamine | + |
| isoamylamine | + |
| propylamine | + |
| isobutylamine | + |
| cyclohexylamine | + |
| heptylamine | + |
| benzylamine | + |
| phenylamine | +P |
| 3-amino-1-propanol | +P |
| 2-aminoethanol | + |
| 4-(aminomethyl) pyridine | +P |
| 4-(2-aminoethyl) morpholine | +P |
| 1-(3-aminopropyl) imidazole | + |
| triphenylphosphine | + |
| 4-(aminopropyl) morpholine | + |
| 9-fluorenemethanol | + |
| p-nitrobenzyl alcohol | + |
| p-(methylthio) benzyl alcohol | + |
| o-aminobenzyl alcohol | + |
| 2-methoxybenzyl alcohol | + |
| 2-(triflouromethyl) benzyl alcohol | + |
| 2-amino-3-phenyl-1-propanol | +P |
| diethylazodicarboxylate | −P |
| 4-dimethylaminopyridine | +P |
| carbazole | + |
| azobenzene | + |
| 3,4-dihydroxybenzoic acid | −P |
| 4-methylmorpholine N-oxide | + |
| 3-cyanobenzoic acid | No flow |
| 4-nitrophenylacetic acid | No flow, at 0.1M, flow occurs lower concentrations (0.01–0.1M) |
| 2-(1H-benzotriazole-1-yl)-1,1,3,3-tetramethyluronium hexafluorophosphate (HBTU) | No flow, at 0.1M, flow occurs lower concentrations (0.01–0.1M) |
| 2,3-dichloro-5,6-dicyano-1,4-benzoquinone | +weak |
| tetrapropylammonium perruthenate | No flow |
| 1-oxo-2,2,6,6-tetramethylpiperdinium chloride | No flow |
| 5-benzimidazolecarboxylic acid | N.D.[b] |
| 4-(aminomethyl) benzoic acid | N.D. |
| 4-(aminomethyl) benzoic acid | N.D. |
| N,N-diisopropylethylamine | N.D. |

-continued

| Reagent | Flow direction* |
|---|---|
| isobuylamine | N.D. |
| glutathione (SH) | N.D. |

*Those directional indicators ("+" or "−") followed by a "P" indicate that flow was achieved using a pulsed voltage program pursuant to FIG. 8, where $\tau_1$ = 0.1–1 ms and $\tau_2$ = 3.0–10 ms.
ᵃ"N.D.", in this table and the tables below, indicates either that the solute was immiscible with the solvent or that visual inspection suggested that it had decomposed.

The following solutions in DCM, at 0.1M unless otherwise indicated, have been tested:

| Reagent | Flow direction* |
|---|---|
| allylamine | − |
| butylamine | − |
| cyclohexylamine | − |
| 1-(3-aminopropyl) imidazole | − |
| diethylazodiacarboxylate | − |
| TP Palladium | − |
| isobutylamine | − |
| isoamylamine | − |
| propylamine | − |
| 1-(3-aminopropyl)imidazole | − |
| p-carboxybenzenesulfonamide | N.D. |
| 2-(1H-benzotriazole-1-yl)-1,1,3,3-tetramethyluronium hexafluorophosphate (HBTU) | N.D. |

*Those directional indicators ("+" or "−") followed by a "P" indicate that flow was achieved using a pulsed voltage program pursuant to FIG. 8, where $\tau_1$ = 0.1–1 ms and $\tau_2$ = 3.0–10 ms.

The following solutions in methanol, all at 0.1 M, have been tested:

| Reagent | Flow direction* |
|---|---|
| 4-fluorophenylacetic acid | − |
| 9-fluorenemethanol | −P |
| p-(methylthio) benzyl alcohol | − |
| (R) sec-phenethyl alcohol | − |
| 3-cyanobenzoic acid | No flow |
| 4-nitrophenylacetic acid | −weak |
| allylamine | No flow |
| 2-aminoethanol | No flow |
| 2-(1H-benzotriazole-1-yl)-1,1,3,3-tetramethyluronium hexafluorophosphate (HBTU) | N.D. |
| isobutylamine | N.D. |
| isomylamine | N.D. |

*Those directional indicators ("+" or "−") followed by a "P" indicate that flow was achieved using a pulsed voltage program pursuant to FIG. 8, where $\tau_1$ = 0.1–1 ms and $\tau_2$ = 3.0–10 ms.

Example 2—An electrode-pump based preferential flow system

Figure 18A:
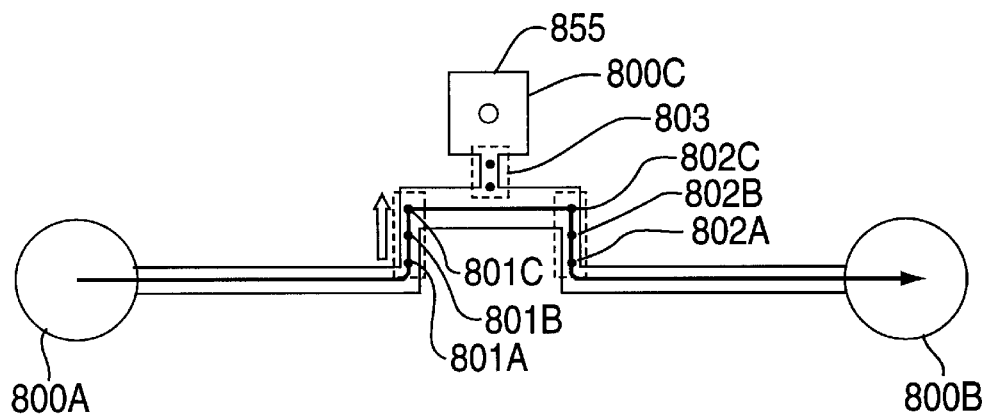
FIGS. 18A and 18B show a channel device having electrode-based pumps.
Figure 18B:
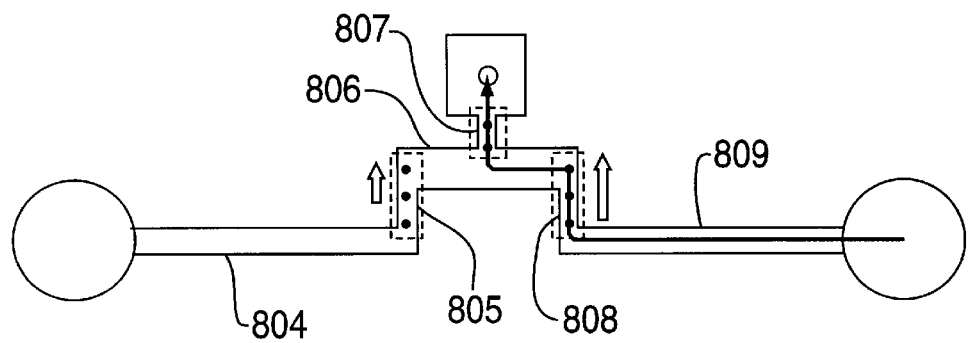

A channel system was fabricated on two inch by two inch by 20 mil plates of 211 Corning glass (Corning Glass Co., Corning, N.Y.) to confirm that liquids can be switched to a desired flow pathway by controlling the voltages applied to certain electrode-based pumps. As illustrated in FIGS. 18A and 18B, first channel 804 (2,600 $\mu$m long by 150 $\mu$m wide by 100 $\mu$m deep), second channel 805 (550 $\mu$m long by 100 $\mu$m wide by 100 $\mu$m deep), third channel 806 (800 $\mu$m long by 275 $\mu$m wide by 100 $\mu$m deep), fourth channel 807 (200 $\mu$m long by 100 $\mu$m wide by 100 $\mu$m deep), fifth channel 808 (550 $\mu$m long by 100 $\mu$m wide by 100 $\mu$m deep) and sixth channel 809 (2,600 $\mu$m long by 150 $\mu$m wide by 100 $\mu$m deep) were fabricated on channel plate 810 (not shown). Also fabricated on the channel plate 810 were first well 800A, second well 800B and third well 800C, which were connected by the channels. An electrode plate 820 was overlaid and sealed to the channel plate 810 by field assisted thermal bonding. The electrode plate 820 had openings into first well 800A and second well 800B (not illustrated). Third well 800C included a center drain 855. The electrode plate 820 further had platinum electrodes, fabricated by inserting 25 $\mu$m wires. The electrodes included first platinum electrode 801A, second platinum electrode 801B, third platinum electrode 801C, fourth platinum electrode 802A, fifth platinum electrode 802B, third platinum electrode 802C, and the two electrodes comprising gamma electrode-based pump 803. First platinum electrode 801A, second platinum electrode 801B and third platinum electrode 801 C make up alpha electrode-based pump 801, while fourth platinum electrode 802A, fifth platinum electrode 802B and sixth electrode 802C make up beta electrode-based pump 802.

FIG. 18A shows methanol flowing from first well 800A to second well 800B, while bypassing third well 800C. This is done by applying 160 V to alpha electrode-based pump 801. FIG. 18B shows methanol flowing from second well 800B to third well 800C while bypassing first well 800A. This is done by applying 200 V to beta electrode-based pump 802, 100 V to gamma electrode-based pump 803 and 120 V to alpha electrode-based pump 801, where the polarity at beta and gamma electrode-based pumps 802 and 803 favored flow into the third well 800C, and the polarity at alpha electrode-based pump 801 favored flow away from first well 800A.

Example 3—Electrode-based pumping past capillary barriers

Figure 19:
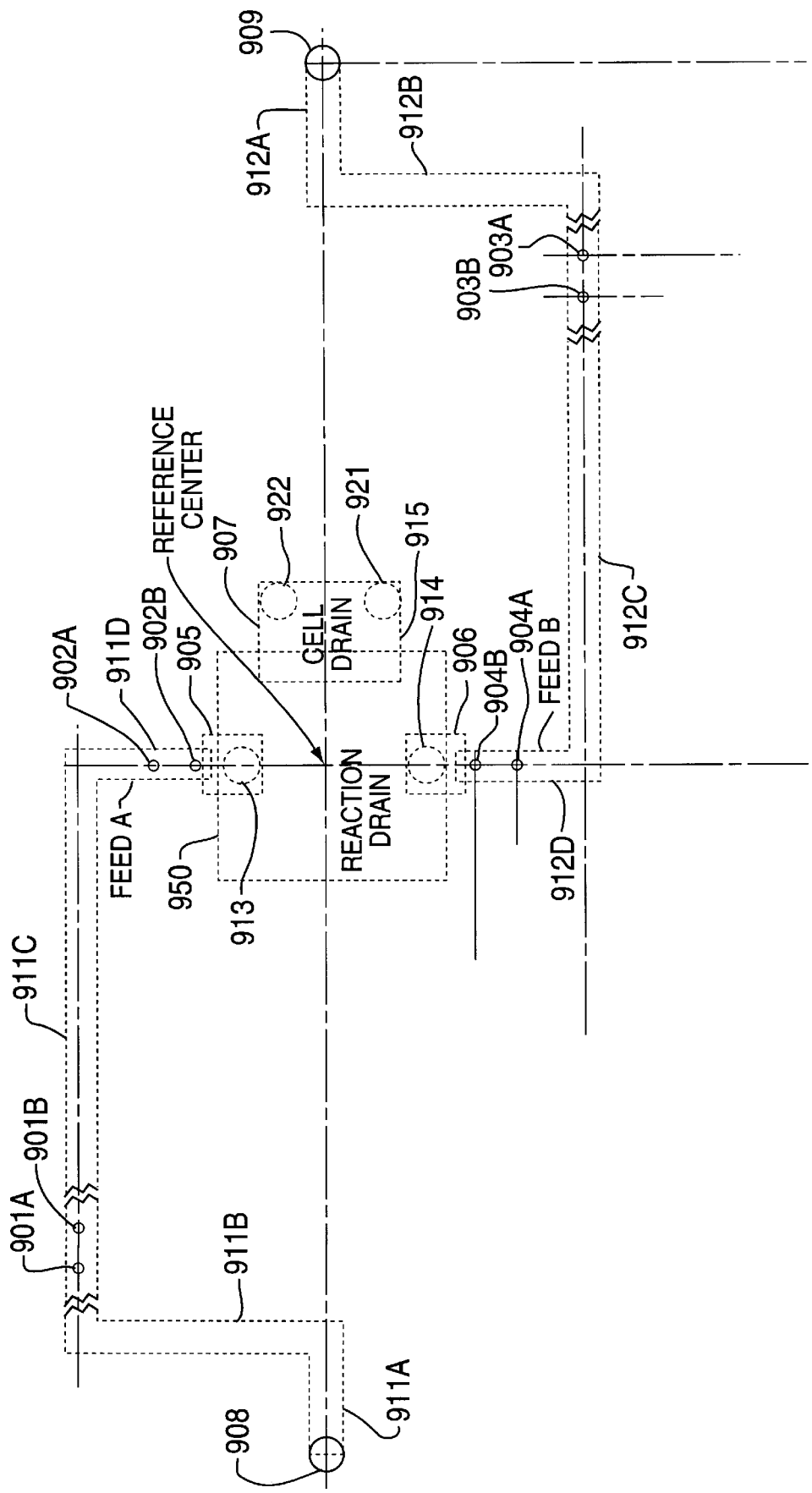
FIG. 19 shows a liquid distribution system design pursuant to the hydrologic liquid distribution system.

FIG. 19 shows a prototype liquid distribution system fabricated pursuant to the hydrologic liquid distribution system. The distribution system was constructed from three plates of Corning 7740 glass, Corning Glass, Inc., Corning, N.Y. which plates became top plate 910, intermediate plate 920 and bottom plate 930. The top of intermediate plate 920 was coated with silicon as described above. In top plate 910 were formed, by laser drilling, first hole 901A, second hole 901B, third hole 902A, fourth hole 902B, fifth hole 903A, sixth hole 903B, seventh hole 904A and eighth hole 904B, which holes each had a diameter of 75 $\mu$m. First and second holes 901A and 901B were used to form first model electrode-based pump 961. Third and fourth holes 902A and 902B were used to form second prototype electrode-based pump 962. Fifth and sixth holes 903A and 903B were used to form third prototype electrode-based pump 963. Seventh and eighth holes 904A and 904B were used to form fourth model prototype electrode-based pump 964. The electrodes in each of first through fourth prototype electrode-based pumps, 961–964, were separated by 200 $\mu$m By etching, alpha opening 905, beta opening 906 and gamma opening 907 were formed on the underside of top plate 910. By laser drilling, ninth hole 908 and tenth hole 909, each with a diameter of 150 $\mu$m, were formed through upper plate 910.

In intermediate plate 920 were formed first prototype channel 911 (made up of segments 911A–911D) and second prototype channel 912 (made up of segments 912A–912D). First and second prototype channels 911 and 912 having a depth of 80 $\mu$m and a width of 150 $\mu$m. The entries into these two prototype channels 911 and 912 are provided by ninth hole 908 and tenth hole 909, respectively. First reaction cell access hole 913 and second reaction cell access hole 914, each with a diameter of 150 $\mu$m, were laser drilled through the intermediate plate 920. In the underside of intermediate plate 920, a delta opening 915 was formed, which delta opening 915 connects the reaction cell 950 to first and second prototype drain holes 921 and 922.

In the bottom plate 930, the reaction cell 950 was formed by etching. First prototype drain hole 921 and second prototype drain hole 922 were laser drilled through bottom plate 920. The top plate 910 and intermediate plate 920 were bonded together by field assisted thermal bonding.

When methanol was introduced into first prototype channel 911, the liquid was stopped from flowing into reaction cell access hole 913 by the capillary barrier formed by the structure at alpha opening 905. Correspondingly, the capillary barrier formed by the structure at beta opening 906 prevented methanol flow into the reaction cell access hole 914. Flow into the reaction cell access holes 913 or 914, by either route, could be initiated by activating the appropriate pumps. For instance, to pump methanol through first prototype channel 911, first prototype electrode-based pump 901 and second prototype electrode-based pump 902 were biased by applying 200 V. Flow through the prototype channel 911 was observed.

Example 4—Combinatorial Synthesis of Oligonucleotide

This synthesis begins with a number of polystyrene beads onto which is synthesized, by the phosphoramidite method, a protected oligonucleotide having a sequence (5' to 3'): GGAGCCATAGGACGAGAG. See, for instance, Caruthers et al., *Methods in Enzymology* 211: 3–20, 1992, for further discussion of oligonucleotide synthetic methods. The functionalized polystyrene beads, available from Bacham Bioscience (King of Prussia, Pa.) are inserted into each of the reaction cells of a microscale liquid distribution system having 4×4 reaction cells. The liquid distribution system has four first reservoirs, reservoir-1, reservoir-2, reservoir-3 and reservoir-4, each of which can address any reaction cell in the 4×4 array. The liquid distribution system has four second reservoirs, reservoir-5, reservoir-6, reservoir-7 and reservoir-8, each of which second reservoirs can address the four reaction cells along a given row (i.e., the reaction cells aligned along an EW axis). Further, the liquid distribution system has four third reservoirs, reservoir-9, reservoir-10, reservoir-11 and reservoir-12, each of which third reservoirs can address any of the four reaction cells in the corresponding column (i.e., reaction cells aligned along an NS axis).

The following process steps are executed:

1. Each of the reaction cells in the distribution system is washed with acetonitrile from reservoir-1.
2. 3% trichloro acetic acid (TCA) in dichloromethane, from reservoir-2, is pumped through all of the reaction cells. This solution is effective to remove the dimethoxytrityl protecting groups at the 5' ends of the oligonucleotides on the beads.
3. All of the reaction cells in the liquid distribution system are again flushed with acetonitrile from reservoir-1.
4. To the four reaction cells connected to reservoir-5, a mixture of 0.1M protected adenine phosphoramidite in acetonitrile is added. This addition is effective to attach protected adenosine groups to the 5' ends of the oligonucleotides in the four reaction cells connected to reservoir-5. To the four reaction cells connected to reservoir-6, a mixture of 0.1M protected cytosine phosphoramidite in acetonitrile is added. This addition is effective to attach protected cytosine groups to the 5' ends of the oligonucleotides in the four reaction cells connected to reservoir-6. To the four reaction cells connected to reservoir-7, a mixture of 0.1M protected guanosine phosphoramidite in acetonitrile is added. This addition is effective to attach protected guanosine groups to the 5' ends of the oligonucleotides in the four reaction cells connected to reservoir-7. To the four reaction cells connected to reservoir-8, a mixture of 0.1M protected thymidine phosphoramidite in acetonitrile is added. This addition is effective to attach protected thymidine groups to the 5' ends of the oligonucleotides in the four reaction cells connected to reservoir-7.
5. The reaction cells are washed with acetonitrile from reaction cells from reservoir-1.
6. The reaction cells are flushed with acetic anhydride:2,6-lutidine:tetrahydrofuran 1:1:8 from reservoir-3. This solution is effective to cap any oligonucleotide chains that did not react with the added monomer.
7. The reaction cells are flushed with 1.1M tetrabutylperoxide in dichloromethane. This step is effective to oxidize the phosphite triester, which links the newly added monomer to the oligonucleotide, to a phosphate triester.
8. Steps 1–3 are repeated.
9. To the four reaction cells connected to reservoir-9, a mixture of 0.1M protected adenine phosphoramidite in acetonitrile is added. This addition is effective to attach protected adenosine groups to the 5' ends of the oligonucleotides in the four reaction cells connected to reservoir-9. To the four reaction cells connected to reservoir-10, a mixture of 0.1M protected cytosine phosphoramidite in acetonitrile is added. This addition is effective to attach protected cytosine groups to the 5' ends of the oligonucleotides in the four reaction cells connected to reservoir-10. To the four reaction cells connected to reservoir-11, a mixture of 0.1M protected guanosine phosphoramidite in acetonitrile is added. This addition is effective to attach protected guanosine groups to the 5' ends of the oligonucleotides in the four reaction cells connected to reservoir- 1. To the four reaction cells connected to reservoir- 2, a mixture of 0.1M protected thymidine phosphoramidite in acetonitrile is added. This addition is effective to attach protected thymidine groups to the 5' ends of the oligonucleotides in the four reaction cells connected to reservoir-12.

The above outlined process is effective to generate 16 separate oligonucleotides, each with a distinct dinucleotide sequence at the 5' end. Similar synthetic methods can be applied to create various combinatorial molecules, including peptides and other molecules such as those having potential pharmacological activity or those useful for diagnostic or other analytical application.

We claim:

1. A liquid distribution system for selectively distributing liquid from two or more liquid sources to a plurality of cells, the system comprising, within a substrate:
   (a) the liquid sources;
   (b) for each liquid source, a channel of capillary dimensions addressable by the liquid source, wherein the channel has at least one outlet to one outlet to one of said cells;
   (c) for each outlet, a capillary barrier interposed between the liquid source and the outlet for inhibiting flow out of the outlet;
   (d) a plurality of electrically operated micropumps, each for pumping liquid through at least one of the capillary barriers, wherein the pumps can be selectively operated such that liquid flows through a capillary barrier when a corresponding micropump is operated.

2. The liquid distribution system of claim 1, wherein at least one said cell can receive liquid from either a first liquid source or a second liquid source depending on the operation of the pumps.

3. The liquid distribution system of claim 1, wherein at least one capillary barrier comprises one or more upwardly oriented sharp edges creating ridges oriented across a direction of liquid flow out of the outlet corresponding to the capillary barrier.

4. The liquid distribution system of claim 1, comprising:
a receiving plate on which the plurality of cells are located, wherein liquids are selectively channeled from the liquid sources to the plurality of cells through the plurality of channels.

5. The liquid distribution system of claim 4, wherein the receiving plate can be releasably positioned below the substrate.

6. The liquid distribution system of claim 1, wherein the micropumps move liquids by means of electrodes.

7. The liquid distribution system of claim 6, wherein the pumps each comprises at least a first and second electrode, and further comprising a controller comprising circuitry for generating and delivering across each first and second electrode pulsed voltages effective to cause pumping.

8. The liquid distribution system of claim 1, wherein the substrate is made of glass, fused silica, quartz or silicon.

9. The liquid distribution system of claim 8, wherein the substrate is made of glass or fused silica.

10. The liquid distribution system of claim 1, wherein the liquid distribution system delivers liquids to at least about 100 sells.

11. A liquid distribution system for selectively distributing liquid from two or more liquid sources to a plurality of cells, the system comprising:
(a) liquid sources;
(b) a substrate comprising a network of fluid channels of capillary dimensions for directing liquid from the liquid sources to a plurality of outlets for outputting liquid at the cells;
(c) pumps that move liquid by means of electrodes for each outlet, wherein the electrodes are incorporated into the substrate, the pumps for selectively pumping liquid from a liquid source and out of the outlet; and
(d) a receiving plate, on which the cells are located, that can be releasably positioned below the distribution plate,
wherein the pumps can be selectively operated, and at least one said cell can receive liquid from either a first liquid source or a second liquid source depending on the operation of the pumps.

12. A liquid distribution system for directing two or more liquids to each of two or more cells comprising:
(a) a distribution substrate comprising sequentially, in order from top to bottom, a first plate, one or more intermediate plates and a second plate, at least one intermediate plate formed of material susceptible to microfabrication methods for forming channels of capillary dimensions on the surface of the plate, each plate having a top and bottom surface, wherein each pair of adjacent top and bottom surfaces are bonded together, and wherein the distribution substrate comprises:
at least two first liquid sources,
at least one first feeder channel segment of capillary dimensions connected to each of the first liquid sources, each first feeder channel segment formed along a first junction between two of the first, second or intermediate plates; and
at least one distribution channel, of capillary dimensions and having an outlet at one or more of said cells, wherein the distribution channel is connected to each feeder channel and formed along a second junction, distinct from the first, of two of the first, second or intermediate plates,
wherein filling each first source with a liquid results in filling connected first feeder channel segments and connected distribution channels, and
wherein distribution channels connected to one first feeder channel segment avoid intersecting with other first feeder channel segments due to being formed along the second junction instead of along the first junction where the first feeder channel segments are formed.

13. The liquid distribution system of claim 12, wherein in the distribution substrate one first feeder channel segment from each of the at least two first liquid sources are parallel and adjacent to one another, and these parallel and adjacent channels define a route for delivering liquid from the each of the first liquid sources to two or more cells.

14. The liquid distribution system of claim 13, wherein each of the parallel first feeder channel segments is connected to a separate distribution channel and each of said connected distribution channels are parallel and adjacent to one another.

15. The liquid distribution system of claim 14, comprising in the distribution substrate at least four first liquid sources and at least two sets of parallel, adjacent feeder channel segments, wherein each such set includes a first feeder channel segment separately connected to each of at least four liquid sources, and wherein each such set of parallel, adjacent first feeder channel segments is connected to at least two sets of adjacent distribution channels, each distribution channel set for delivering liquid to at least one cell, wherein each such set of first feeder channel segments can deliver liquid from any of four liquid sources to at least two separate cells.

16. The liquid distribution system of claim 13, wherein in the distribution substrate the first feeder channel segments connected to the first liquid sources are substantially parallel to one another and wherein the distribution substrate comprises:
one or more second liquid sources ;and
at least one second feeder channel segment connected to each second liquid source such that the second liquid sources each address at least one cell via a second feeder channel segment,
wherein each second feeder channel segment is formed along a junction between plates distinct from a junction along which the first feeder channel segments are formed, wherein first and second feeder channel segments would intersect but for being formed along such separate junctions.

17. The liquid distribution system of claims 16, wherein the second feeder channel segments are substantially perpendicular to the first feeder channel segments.

18. The liquid distribution system of claim 17, further comprising one or more intermediary channels that connect feeder channel segments to said cells, wherein at least one intermediary channel is positioned adjacent to and receives liquid from at least two first distribution channels and at least one second feeder channel segment.

19. The liquid distribution system of claimed 13, further comprising:

(b) electrically operated micropumps embedded in the distribution substrate for regulating the flow of liquid through channels;

(c) a controller for controlling the micropumps so that liquids can be selectively directed to said cells, wherein the first plate comprises supply channels extending through the first plate to the first liquid sources and electrical leads extending through the first plate, wherein micropumps are located at each distribution channel and are connected to and operated by means of the controller by the electrical leads extending through the first plate.

20. The liquid distribution system of claim 19, further comprising:

(d) a receiving plate having one or more cells that can be releasably positioned below the second plate, wherein the distribution substrate comprises conduits at the cells by which liquid can be moved from the distribution channels to the cells under the control of the pumps.

21. The liquid distribution system of claim 20, wherein the conduits include capillary barriers.

22. The liquid distribution system of claim 19, wherein the micropumps move liquids by means of electrodes.

23. The liquid distribution system of claim 22, wherein the electrical leads through the first plate are made of fused via ink, and wherein the electrodes of the micropumps are formed by plating metal on the ends of the electrical leads.

24. The liquid distribution system of claim 22, wherein the micropumps in the distribution substrate each comprise at least a first electrode and a second electrode and the controller comprises circuitry for generating and delivering across each first and second electrode pair pulsed voltages effective to cause pumping.

25. The liquid distribution system of claim 24, wherein the controller comprises an electrical data storage device comprising a database of pumping programs for pumping from each of a plurality of uniform micropumps a plurality of liquids.

26. The liquid distribution system of claim 25, wherein the programs are for pumping reagents utilized in a synthetic reaction.

27. The liquid distribution system of claim 26, wherein the reagents are selected from the group consisting of a carboxylic acid, a carbodiimide, a sulfonamide, an amine, an alcohol, a pyridine, an azodicarboxylate, a carbazole, an azobenzene, an amino N-oxide, a 1,4-benzoquinone and an ammonium perruthenate.

28. The liquid distribution system of claim 24, wherein one or more of the pumps further comprise a third electrode, wherein for such pumps with three electrodes, a first pair of electrodes are operated to pump fluids of low conductivity and a second pair of electrodes, which are more widely separated than the first pair, are operated to pump fluids of higher conductivity, wherein the first pair pumps tetrahydrofuran more effectively than the second pair.

29. The liquid distribution system of claim 28, wherein the controller directs direct a pulsed voltage (i) across the first pair of electrodes to pump liquid or (ii) across the second pair of electrodes to pump liquid.

30. The liquid distribution system of claim 29, wherein the controller operates the electrode-based pumps by directing between about 50 and about 2,000 V to the electrode-based pumps.

31. The liquid distribution system of claim 12, wherein the plates are made of glass, fused silica, quartz or silicon.

32. The liquid distribution system of claim 31, wherein the plates are made of glass or fused silica.

33. The liquid distribution system of claim 12, wherein the liquid distribution system delivers liquids to at least about 100 cells.

34. A liquid distribution system comprising an alpha liquid source, a beta liquid source and a system of channels of capillary dimensions having a plurality of outlets for delivering liquid to a plurality of cells, wherein the liquid sources and the system are formed within a substrate, the system comprising:

(A) a first set of parallel and adjacent first and second capillary feeder channels; and (B) a second set of parallel and adjacent third and fourth capillary feeder channels which are offset from the first and second feeder channels, wherein each said feeder channel has a plurality of outlets, and wherein (a) the first and third feeder channels are connected to the alpha liquid source by a first capillary connector channel that is situated above or below the second and fourth feeder channels and are independent of the beta liquid source and (b) the second and fourth feeder channels are connected to the beta liquid source by a second capillary connector channel that is situated above or below the first and third feeder channels and are independent of the alpha liquid source, wherein upon filling the alpha liquid source with a liquid the first and second feeder channels are filled via the first connector channel and wherein upon filling the beta liquid source with a liquid the third and fourth feeder channels are filled via the second connector channel.

35. The liquid distribution system of claim 34, wherein the system further comprises:

(C) valves for controlling the flow of fluids out of the outlets, and wherein the outlets from the first and second feeder channels are connected to each cell of a first set of two or more cells and the outlets from the third and fourth feeder channels are connected to each cell of a second set of two or more reaction cells, so that the cells of the first set or the second set can receive fluid liquid from either the alpha liquid source or the beta liquid source.

36. The liquid distribution system of claim 35, wherein the feeder channels of the first and second feeder channel sets are parallel to each other.

37. The liquid distribution system of claim 34, wherein the substrate is made of glass, fused silica, quartz or silicon.

38. The liquid distribution system of claim 37, wherein the substrate is made of glass or fused silica.

39. The liquid distribution system of claim 34, wherein the liquid distribution system delivers liquids to at least about 100 cells.

40. A liquid distribution system for selectively distributing liquid from two or more liquid sources to a plurality of cells, the system comprising a cell, a channel of capillary dimensions connected to the cell and a pump situated in the channel comprising a first pair of electrodes and a second pair of electrodes, wherein one electrode can be shared between the two pairs, wherein the first pair has a spacing between the electrodes selected for pumping liquids of a low polarity and the second pair has a wider spacing selected for pumping liquids of relatively higher polarity, and wherein the first pair pumps tetrahydrofuran more effectively than the second pair, wherein the electrodes comprise electrical leads made of fused via ink and having an end that intersects the channel, wherein channel intersecting ends of the leads are plated with metal.

41. The liquid distribution system of claim 40, wherein the electrodes of the first pair are spaced between about 100 microns and 2500 microns apart.

42. The liquid distribution system of claim 41, wherein the spacing of the second pair of electrodes is between about 200 microns and 5000 microns.

43. The liquid distribution system of claim 40, wherein the first electrode and second electrode are spaced between about 250 microns and 1000 microns apart.

44. The liquid distribution system of claim 43, wherein the spacing of the second pair of electrodes is between about 500 microns and 1500 microns.

45. The liquid distribution system of claim 40, further comprising a controller that controls the operation of the pump, wherein the controller comprises circuitry to operate any pair of electrodes in the pump, wherein the controller comprises an information storage means which stores pumping protocols for one or more liquids, each of which stored protocols include a designation of an appropriate pair of pump electrodes for pumping a liquid.

46. A liquid distribution system for selectively distributing liquid from two or more liquid sources to a plurality of cells, the system comprising:
within a substrate, one or more feeder channels of capillary dimensions each made up of a feeder channel inlet and a feeder channel outlet and, connected to each such feeder channel, a distribution channel, each feeder channel having a three-way junction connecting the feeder channel inlet, the feeder channel outlet and the connected distribution channel, the distribution channel connecting with a cell;
within the substrate, for each such three-way junction, a first pump, which moves liquid by means of electrodes, located in the feeder channel inlet or in the feeder channel outlet;
within the substrate, for each such three-way junction, a second electrode-based pump, which moves liquid by means of electrodes, located in the distribution channel; and
a controller comprising circuitry for generating and selectively delivering voltages across two electrodes of each first pump and two electrodes of each second pump so that (a) fluid in one of the feeder channels can be moved from the feeder channel inlet to the feeder channel outlet of the feeder channel with a first amount of flow into the connected distribution channel or (b) a second amount of flow which is greater than the first amount proceeds via the connected distribution channel.

47. The liquid distribution system of claim 46, wherein for at least one such three-way junction there is a third pump which moves liquid by means of electrodes, located in whichever of the feeder channel inlet or feeder channel outlet lacks the first electrode-based pump.

48. The liquid distribution system of claim 46, wherein one or more distribution channels have a capillary barrier placed in a path of flow from a liquid source to a cell which stops liquid flow in the absence of pumping pressure from the second electrode-based pump.

49. The liquid distribution system of claim 46, wherein the opening of one or more distribution channels at the three-way junction has a width that is about 50% or less of the width of the connected feeder channel.

50. The liquid distribution system of claim 46, wherein the controller comprises circuitry for generating and selectively delivering pulsed voltages effective to cause pumping to the first and second pumps.

51. A liquid distribution system comprising:
at least one cell,
two or more feeder channels of capillary dimensions,
a separate conduit for each feeder channel connecting that feeder channel to the cell, and
a expansion valve for each conduit, the expansion valve comprising an expandable fluid enclosed within an expandable container, wherein the expansion valve has an expanded state that fills a cross-section of the conduit to prevent fluid flow through the conduit and a contracted state that does not fill a cross-section of the conduit so that flows through the conduit.

52. The liquid distribution system of claim 51 further comprising at least about two cells, each separately addressable by two or more feeder channels via conduits each having a expansion valve.

53. The liquid distribution system of claim 51, wherein at least one conduit has two or more expansion valves.

54. The liquid distribution system of claim 53, wherein at least one conduit has three or more expansion valves are positioned in the conduit so that they can be operated in concert to pump liquid from the connected feeder channel into the cell.

55. A liquid distribution system comprising:
one or more continuous flow channels of capillary dimensions, each having an upstream end and a downstream end, wherein the continuous flow channels have an open zone at the downstream end,
for each continuous flow channel, a branch channel extending off of that continuous flow channel in the open zone, and
for each continuous flow channel, an electronically operable alpha constrictor for constricting flow in the open zone located downstream of the branch channel inlet,
wherein when a liquid flows through one of the continuous flow channels from the upstream to the downstream end a first ratio amount of fluid is diverted into the branch channel when the alpha constrictor is not operating and a second ratio amount, which is greater than the first ratio amount, flows into the branch channel when the alpha constrictor is in operation.

56. The liquid distribution system of claim 55, further comprising, for at least one branch channel, an electronically operable beta constrictor for constricting flow through the branch channel.

57. The liquid distribution system of claim 55, wherein the system has two or more continuous flow channels and further comprising a buffer channel addressable by at least two continuous flow channels via their associated branch channels.

58. The liquid distribution system of claim 57, further comprising a reaction cell and wherein the buffer channel is connected to a reaction cell conduit to the reaction cell and to an overflow conduit.

59. The liquid distribution system of claim 58, wherein the reaction cell conduit has an electronically operable gamma constrictor and the overflow conduit has an electronically operable delta constrictor.

\* \* \* \* \*